US009023848B2

(12) United States Patent
Flynn et al.

(10) Patent No.: US 9,023,848 B2
(45) Date of Patent: May 5, 2015

(54) SMALL-MOLECULES AS THERAPEUTICS

(75) Inventors: Bernard Luke Flynn, Donvale (AU); Dharam Paul, Flinders Park (AU); Andrew John Harvey, Goodwood (AU); Damian Wojciech Grobelny, Watsonia North (AU); Sue O'Connor, Prospect (AU); Jonathan Bayldon Baell, Ivanhoe (AU); Brad Sleebs, Bundoora (AU); Ian Phillip Street, Macleod (AU)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 14/002,243

(22) PCT Filed: Mar. 2, 2012

(86) PCT No.: PCT/AU2012/000223
§ 371 (c)(1),
(2), (4) Date: Dec. 12, 2013

(87) PCT Pub. No.: WO2012/116415
PCT Pub. Date: Sep. 7, 2012

(65) Prior Publication Data
US 2014/0088104 A1    Mar. 27, 2014

(51) Int. Cl.
C07D 215/54     (2006.01)
C07D 215/38     (2006.01)
C07D 401/04     (2006.01)
C07D 413/04     (2006.01)
C07D 491/107    (2006.01)

(52) U.S. Cl.
CPC ............ *C07D 215/54* (2013.01); *C07D 215/38* (2013.01); *C07D 401/04* (2013.01); *C07D 413/04* (2013.01); *C07D 491/107* (2013.01)

(58) Field of Classification Search
None
See application file for complete search history.

(56) References Cited

U.S. PATENT DOCUMENTS

| | | |
|---|---|---|
| 3,429,887 A | 2/1969 | Lesher et al. |
| 4,404,201 A | 9/1983 | Haskell et al. |
| 5,095,015 A | 3/1992 | Albaugh |
| 5,182,290 A | 1/1993 | Albaugh |
| 5,182,386 A | 1/1993 | Albaugh et al. |
| 5,212,310 A | 5/1993 | Thurkauf et al. |
| 5,306,819 A | 4/1994 | Albaugh et al. |
| 5,312,822 A | 5/1994 | Albaugh |
| 5,328,912 A | 7/1994 | Albaugh |
| 5,451,585 A | 9/1995 | Albaugh |
| 5,473,073 A | 12/1995 | Albaugh et al. |
| 5,484,944 A | 1/1996 | Albaugh et al. |
| 5,510,480 A | 4/1996 | Albaugh |
| 5,608,079 A | 3/1997 | Albaugh et al. |
| 5,625,063 A | 4/1997 | Thurkauf et al. |
| 5,723,462 A | 3/1998 | Albaugh et al. |
| 5,750,702 A | 5/1998 | Albaugh et al. |
| 5,804,686 A | 9/1998 | Albaugh et al. |
| 5,817,813 A | 10/1998 | Thurkauf et al. |
| 5,925,770 A | 7/1999 | Albaugh et al. |
| 6,013,650 A | 1/2000 | Thurkauf et al. |
| 6,080,873 A | 6/2000 | Albaugh et al. |
| 6,096,887 A | 8/2000 | Albaugh et al. |
| 6,143,760 A | 11/2000 | Albaugh et al. |
| 6,166,203 A | 12/2000 | Cai et al. |
| 6,177,569 B1 | 1/2001 | Rachwal et al. |
| 6,211,365 B1 | 4/2001 | Albaugh et al. |
| 6,229,017 B1 | 5/2001 | Lui et al. |
| 6,297,256 B1 | 10/2001 | Cai et al. |
| 6,353,109 B1 | 3/2002 | Albaugh et al. |
| 6,399,604 B1 | 6/2002 | Albaugh et al. |
| 6,413,956 B1 | 7/2002 | Albaugh et al. |
| 6,414,147 B1 | 7/2002 | Currie et al. |
| 6,423,711 B1 | 7/2002 | Cai et al. |
| 6,423,956 B1 | 7/2002 | Mandella et al. |
| 6,511,987 B1 | 1/2003 | Yuan et al. |
| 6,515,140 B2 | 2/2003 | Albaugh et al. |

(Continued)

FOREIGN PATENT DOCUMENTS

| | | |
|---|---|---|
| AU | 2005204365 A1 | 8/2005 |
| AU | 2005209367 A1 | 8/2005 |

(Continued)

OTHER PUBLICATIONS

International Search Report and Written Opinion for PCT/AU2007/001566 mailed Nov. 20, 2007.
International Preliminary Report on Patentability for PCT/AU2007/001566, completed Oct. 1, 2008.
International Search Report and Written Opinion for PCT/AU2012/000223 mailed Apr. 4, 2012.
International Preliminary Report on Patentability for PCT/AU2012/000223, mailed Sep. 12, 2013.
International Search Report and Written Opinion for PCT/AU2012/000216 mailed Mar. 15, 2012.
International Preliminary Report on Patentability for PCT/AU2012/000216, mailed Sep. 12, 2013.

(Continued)

*Primary Examiner* — Timothy R Rozof
(74) *Attorney, Agent, or Firm* — Wolf, Greenfield & Sacks, P.C.

(57) ABSTRACT

The present invention provides compounds of formula (I), pharmaceutically acceptable salts thereof, and pharmaceutical compositions thereof. Compounds of the present invention are useful in treating central nervous system disorders, such as anxiety disorders or depression.

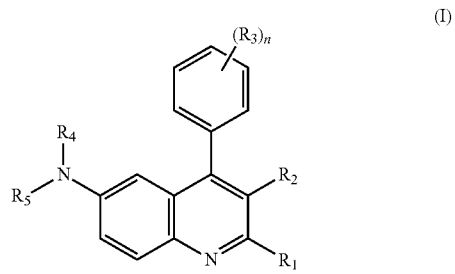

19 Claims, No Drawings

(56) References Cited

U.S. PATENT DOCUMENTS

| | | |
|---|---|---|
| 6,559,163 B2 | 5/2003 | Cai et al. |
| 6,646,124 B2 | 11/2003 | Albaugh et al. |
| 6,656,941 B2 | 12/2003 | Maynard et al. |
| 6,703,393 B2 | 3/2004 | Li et al. |
| 6,720,339 B2 | 4/2004 | Albaugh et al. |
| 6,723,332 B2 | 4/2004 | Cai et al. |
| 6,828,329 B2 | 12/2004 | Cai et al. |
| 8,293,737 B2 | 10/2012 | Baell et al. |
| 8,551,990 B2 | 10/2013 | Baell et al. |
| 8,614,212 B2 | 12/2013 | Baell et al. |
| 2002/0151591 A1 | 10/2002 | Villalobos et al. |
| 2004/0082555 A1 | 4/2004 | Villalobos |
| 2005/0009861 A1 | 1/2005 | Villalobos et al. |
| 2005/0182085 A1 | 8/2005 | Defossa et al. |
| 2005/0182086 A1 | 8/2005 | Defossa et al. |
| 2005/0182087 A1 | 8/2005 | Defossa et al. |
| 2014/0045839 A1 | 2/2014 | Baell et al. |
| 2014/0051701 A1 | 2/2014 | O'Connor et al. |

FOREIGN PATENT DOCUMENTS

| | | |
|---|---|---|
| AU | 2005209368 A1 | 8/2005 |
| CA | 1114822 A | 12/1981 |
| EP | 0 341990 A2 | 11/1989 |
| EP | 0 531958 A1 | 3/1999 |
| JP | 50-023036 B | 8/1975 |
| JP | 50-023037 B | 8/1975 |
| JP | 51-032594 A | 3/1976 |
| JP | 55-111486 A | 8/1980 |
| JP | 55-151584 A | 11/1980 |
| JP | 56-115787 A | 9/1981 |
| JP | 56-118081 A | 9/1981 |
| JP | 56-118083 A | 9/1981 |
| JP | 57-026688 A | 2/1982 |
| JP | 57-109790 A | 7/1982 |
| JP | 59-093080 A | 5/1984 |
| JP | 2002-544197 A | 12/2004 |
| JP | 2005-162726 A | 6/2005 |
| JP | 2006-508989 A | 3/2006 |
| WO | WO 00/68202 A1 | 11/2000 |
| WO | WO 02/060872 A1 | 8/2002 |
| WO | WO 02/069948 A1 | 9/2002 |
| WO | WO 03/045313 A2 | 6/2003 |
| WO | WO 03/045920 A1 | 6/2003 |
| WO | WO 03/097564 A2 | 11/2003 |
| WO | WO 2004/048374 A1 | 6/2004 |
| WO | WO 2004/058144 A2 | 7/2004 |
| WO | WO 2004/064721 A2 | 8/2004 |
| WO | WO 2004/083207 A1 | 9/2004 |
| WO | WO 2005/073229 A1 | 8/2005 |
| WO | WO 2005/073230 A1 | 8/2005 |
| WO | WO 2005/073231 A1 | 8/2005 |
| WO | WO 2005/097750 A1 | 10/2005 |
| WO | WO 2006/048146 A2 | 5/2006 |
| WO | WO 2006/060390 A1 | 6/2006 |
| WO | WO 2006/128802 A2 | 12/2006 |
| WO | WO 2007/039172 A1 | 4/2007 |
| WO | WO 2008/021210 A2 | 2/2008 |
| WO | WO 2008/046135 A1 | 4/2008 |
| WO | WO 2010/135360 A1 | 11/2010 |
| WO | WO 2012/116410 A1 | 9/2012 |
| WO | WO 2012/116415 A1 | 9/2012 |
| WO | WO 2012/151640 A1 | 11/2012 |

OTHER PUBLICATIONS

International Search Report and Written Opinion for PCT/AU2012/000533 mailed May 31, 2012.
International Preliminary Report on Patentability for PCT/AU2012/000533, mailed Nov. 21, 2013.
International Search Report and Written Opinion for PCT/AU2013/000991, mailed Oct. 11, 2013.
[No Author Listed] Mayo Clinc, "Anxiety." Available at http://www.mayoclinic.com/health/anxiety/DS01187. Last accessed Jan. 4, 2012.
[No Author Listed] Medline Plus, "Autoimmune disorders," National Institutes of Health. Available at http://www.nlm.nih.gov/medlineplus/ency/article/000816.html. Last accessed Jun. 3, 2011.
Abdel-Magid et al., Reductive Amination of Aldehydes and Ketones with Sodium Triacetoxyborohydride. Studies on Direct and Indirect Reductive Amination Procedures(1). J Org Chem. May 31, 1996 ; 61(11) :3849-3862.
Berge et al., Pharmaceutical salts. J Pharm Sci. Jan. 1977;66(1):1-19.
Castagné et al., Early behavioral screening for antidepressants and anxiolytics. Drug Dev Res. 2006;67(9):729-742.
Chopin et al., The benzodiazepine antagonist flumazenil blocks the effects of CCK receptor agonists and antagonists in the elevated plus-maze. Psychopharmacology (Berl). 1993;110(4):409-14.
Chung et al., Trimethylaluminium-Facilitated Direct Amidation of Carboxylic Acids. Synlett. 2011;14:2072-2074.
Collini et al., The solid phase synthesis of tri-substituted indoles. Tetrahedron Lett. 1997;38(46): 7963-66.
Cryan et al., The age of anxiety: role of animal models of anxiolytic action in drug discovery. Br J Pharmacol. Oct. 2011;164(4):1129-61. doi: 10.1111/j.1476-5381.2011.01362.x.
Fassold et al., A new assay for nerve fiber repulsion. Ann N Y Acad Sci. Apr. 2010;1193:43-7. doi: 10.1111/j.1749-6632.2009.05295.x.
Flynn et al., A novel palladium-mediated coupling approach to 2,3-disubstituted benzo(b)thiophenes and its application to the synthesis of tubulin binding agents. Org Lett. Mar. 8, 2001;3(5):651-4.
Gezginci et al., Antimycobacterial activity of substituted isosteres of pyridine- and pyrazinecarboxylic acids. 2. J Med Chem. May 10, 2001;44(10):1560-3.
Han et al., Solid phase parallel synthesis of highly substituted thiophene derivatives and identification of novel phosphodiesterase-4 (PDE-4) inhibitors. Tetrahedron. 1999;55(39):11669-85.
Heindl et al., Studies on the antibacterial activity of quinolone carboxylic acids. IX. Aza analogs. Di- and trisubstituted 1,4-dihydro-4-oxo-1, 5-naphthyridine-3 carboxylic acids and 1-ethyl-4-pyridone-3 carboxylic acids. European Journal of Medicinal Chemistry. 1977;12(6):549-55. German.
Heinrichs et al., Brain penetrance, receptor occupancy and antistress in vivo efficacy of a small molecule corticotropin releasing factor type I receptor selective antagonist. Neuropsychopharmacology. Aug. 2002;27(2):194-202.
Johnson et al., Solid phase chemistry approach to the SAR development of a novel class of active site-directed thrombin inhibitors. Tetrahedron. 1999;55:11641-52.
Kaffy et al., Synthesis and biological evaluation of vinylogous combretastatin A-4 derivatives. Org Biomol Chem. Jul. 21, 2005;3(14):2657-60. Epub Jun. 21, 2005.
Maslankiewicz et al., Synthesis and Amination of 4-Chloro-3-quinolinesulfonyl Chloride. Heterocycles. 1994;38(6):1317-31.
Maslankiewicz, From Haloquinolines and Halopyridines to Quinoline- and Pyridinesulfonyl Chlorides and Sulfonamides. Heterocycles. 2007;71(9):1975-90.
Nishimura et al., Conformational analysis of tandospirone in aqueous solution: lead evolution of potent dopamine D4 receptor ligands. Bioorg Med Chem Lett. May 7, 2001;11(9):1141-4.
Pettit et al., Antineoplastic agents 322. Synthesis of combretastatin A-4 prodrugs. Anticancer Drug Des. Jun. 1995;10(4):299-309.
Porsolt et al., Behavioural despair in rats: a new model sensitive to antidepressant treatments. Eur J Pharmacol. Feb. 15, 1978;47(4):379-91.
Soskic et al., QSAR study of 1,8-naphthyridin-4-ones as inhibitors of photosystem II. J Chem Inf Comput Sci. Sep.-Oct. 2001;41(5):1316-21.
Temple et al., Synthesis of potential antimalarial agents. VIII. Azaquinolines. II. Preparation of some 1,5-Naphthyridines and pyrido[3,2-d]pyrimidines. J Heterocyclic Chem. 1970;7(5):1219-22. Abstract Only.
Vercek et al., Heterocycles. 182. Neighboring group interaction in ortho-substituted heterocycles. 2. 1,2,4-Oxadiazolylpyridines and pyrido[2,3-d]pyrimidine 3-oxides. J Org Chem. 1979 ;44(10):1695-1699.

SMALL-MOLECULES AS THERAPEUTICS

RELATED APPLICATION

This application is a national stage filing under 35 U.S.C. §371 of international PCT application, PCT/AU2012/000223, filed Mar. 2, 2012, which claims the benefit of Australian Patent Application No. 2011900738, filed 2 Mar., 2011, each of which is hereby incorporated by reference in its entirety.

FIELD OF THE INVENTION

The present invention relates generally to chemical compounds and methods for their use in therapy and their preparation. In particular, the invention relates to chemical compounds which may possess useful therapeutic activity in a range of central nervous system disorders, and in particular, anxiety disorders and depression. The invention also relates to the use of these compounds in methods of therapy and the manufacture of medicaments as well as compositions containing these compounds.

BACKGROUND OF THE INVENTION

The most widely studied and characterised class of allosteric modulators of the GABA-$GABA_A$ receptor complex are a class of compounds known as benzodiazepines (an example of which is diazepam, a 1,4-benzodiazepine, commonly known as Valium®) which interact with the benzodiazepine (BZ)-site on the $GABA_A$ receptor. Possession of a γ subunit and a particular type of α subunit (1, 2, 3, or 5) is required to confer sensitivity to this class of compounds.

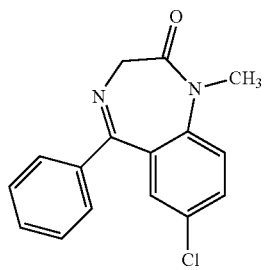

Diazepam

Classical benzodiazepines do not directly open the ion channel, rather they allosterically modify the $GABA_A$ receptor upon binding, potentiating the effect of GABA binding when there is a submaximal concentration of GABA present and thereby increasing hyperpolarizing responses and neuronal inhibition. Benzodiazepines produce systemic effects that include sedation, amnesia, muscle relaxation, and anxiolysis. Hence, these compounds are widely used as anxiolytics, sedative-hypnotics, muscle relaxants, and anti-convulsants. Although the $GABA_A$ binding site is called the benzodiazepine site, drugs of other types can also bind and allosterically modify the receptor at that site. These include drugs with β-carboline, imidazopyridine, and triazolopyridazine structures. It is believed that compounds acting as BZ agonists at $α_1βγ_2$, $α_2βγ_2$ or $α_3βγ_2$ subtypes will possess desirable anxiolytic activity. Such modulators of the BZ binding site of $GABA_A$ are known herein as "$GABA_A$ receptor agonists".

However, while the 1,4-benzodiazepines are an effective class of anxiolytics they possess the often unwanted side-effect of sedation, ataxia, tolerance, withdrawal, memory impairment and addiction. It is postulated that at least some of the unwanted sedation experienced by known anxiolytic drugs which act through the BZ binding site is mediated through $GABA_A$ receptors containing the $α_1$-subunit. This has been determined primarily from the effects displayed by the well studied hypnotic agents Alpidem and Zolpidem which are $α_1$-selective $GABA_A$ receptor agonists.

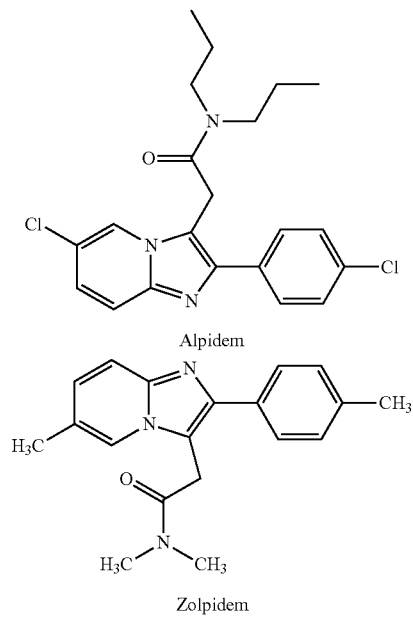

Alpidem

Zolpidem

SUMMARY OF THE INVENTION

The present invention provides compounds of formula (I) and salts thereof;

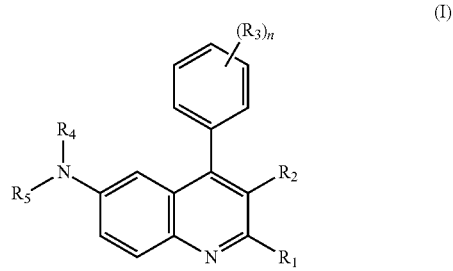

(I)

wherein $R_1$ represents hydrogen, or optionally substituted $C_1$-$C_6$ alkyl;

$R_2$ represents —C(O)NR'R" (where R' is —H or optionally substituted $C_1$-$C_6$ alkyl and R" is optionally substituted $C_1$-$C_6$ alkyl, —OH or —CN, or R' and R" together form an optionally substituted heterocyclyl), —C(O)OR' (where R' is —H or optionally substituted $C_1$-$C_6$ alkyl), —C(O)NHSO$_2$R''' (where R''' is optionally substituted aryl or optionally substituted $C_1$-$C_6$ alkyl), —S(O)$_2$NHR'''' (where R'''' is —H, optionally substituted $C_1$-$C_6$ alkyl, or optionally substituted aryl), optionally substituted heteroaryl or optionally substituted heterocyclyl;

$R_3$ represents carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, or optionally substituted thioacylamino;

$R_4$ represents H, optionally substituted alkyl, optionally substituted aryl, optionally substituted cycloalkyl, optionally substituted acyl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl;

$R_5$ represents optionally substituted cycloalkyl or optionally substituted cycloalkenyl; and n is 0 or an integer of 1 to 4, inclusive.

The present invention also provides pharmaceutical compositions comprising a compound of formula (I) and optionally a pharmaceutically acceptable excipient.

The present invention also provides a method for treating central nervous system disorders, such as anxiety disorders and/or depression, comprising the step of administering to a patient in need thereof a compound of formula (I) or a pharmaceutically acceptable salt thereof;

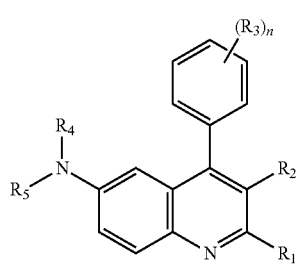

wherein $R_1$, $R_2$, $R_3$, $R_4$, $R_5$, and n are as described herein.

The present invention also provides the use of a compound of formula (I) or a salt thereof:

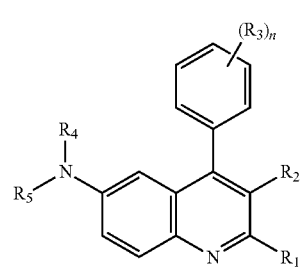

wherein $R_1$, $R_2$, $R_3$, $R_4$, $R_5$, and n are as described herein, in the manufacture of a medicament for the treatment of central nervous system disorders, such as anxiety disorders and/or depression.

The present invention also provides the use of a compound of formula (I) or a salt thereof:

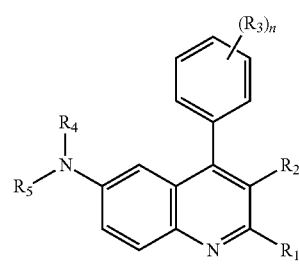

wherein $R_1$, $R_2$, $R_3$, $R_4$, $R_5$, and n are as described herein, for the treatment of central nervous system disorders, such as anxiety disorders and/or depression.

DETAILED DESCRIPTION OF THE INVENTION

The invention is based on the discovery that the compounds of the general formula (I), as described in the above Summary of the Invention have useful properties as possible ligands for biological receptors and biological targets that elicit an effect on the central nervous system. Such compounds have significant potential for the treatment of a variety of disorders of the central nervous system, and in particular affective disorders, for example, anxiety and depression.

"Alkyl" refers to a saturated monovalent hydrocarbon radical which may be straight chained or branched and preferably have from 1 to 10 carbon atoms or more preferably 1 to 6 carbon atoms or 1 to 9 carbon atoms (i.e., $C_1$-$C_4$ alkyl). Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent hydrocarbon radical with at least one site of unsaturation, i.e., a carbon-carbon, $sp^2$ double bond, which may be straight chained or branched and preferably have from 2 to 10 carbon atoms and more preferably 2 to 6 carbon atoms and have at least 1 and preferably from 1-2, carbon to carbon, double bonds. An alkenyl radical includes radicals having "cis" and "trans" orientations, or alternatively, "E" and "Z" orientations. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenyloxy" refers to the group alkenyl-O— wherein the alkenyl group is as described above.

"Alkynyl" refers to a linear or branched monovalent hydrocarbon radical with at least one site of unsaturation, i.e., a carbon-carbon sp triple bond, preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups is as described above.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR$^A$R$^A$ where each R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR$^A$R$^A$ where each R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR$^A$C(O)R$^A$ where each R$^A$ is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR$^A$-alkyl, —OC(O)NR$^A$-aryl, —OC(O)NR$^A$-heteroaryl, and —OC(O)NR$^A$-heterocyclyl where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR$^A$C(O)O-alkyl, —NR$^A$C(O)O-aryl, —NR$^A$C(O)O-heteroaryl, and NR$^A$C(O)O-heterocyclyl where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR$^A$)—R$^A$ where each R$^A$ is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR$^A$)—R$^A$ where each R$^A$ is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR$^A$)—OR$^A$ where each R$^A$ is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like. The term also includes polycyclic ring systems where the cycloalkyl ring is fused with one or more aromatic or non-aromatic carbocyclic or heterocyclic rings, such as adamantanyl, indanyl, 1,2,3,4-tetrahydronapthalenyl and the like.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Halo" or "halogen" refers to fluoro, chloro, bromo and iodo.

"Heteroaryl" refers to a monovalent aromatic heterocyclic group which fulfills the Hückel criteria for aromaticity (ie. contains 4n+2 π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl). It will be understood that where, for instance, R$_2$ is an optionally substituted heteroaryl which has one or more ring heteroatoms, the heteroaryl group can be connected to the core molecule of the compounds of the present invention, through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. In some embodiments, the heteroatom is nitrogen. It will be understood that where, for instance, R$_2$ is an optionally substituted heterocyclyl which has one or more ring heteroatoms, the heterocyclyl group can be connected to the core molecule of the compounds of the present invention, through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR$^A$—P(O)(R$^B$)(OR$^C$) where R$^A$ represents H, alkyl, cycloalkyl, alkenyl, or aryl, R$^B$ represents OR$^C$ or is hydroxy or amino and R$^C$ is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR$^A$—, alkyl-S(O)—NR$^A$—, cycloalkyl-S(O)—NR$^A$—, aryl-S(O)—NR$^A$—, heteroaryl-S(O)—NR$^A$—, and heterocyclyl-S(O)—NR$^A$—, where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR$^A$—, alkyl-S(O)$_2$—NR$^A$—, cycloalkyl-S(O)$_2$—NR$^A$—, aryl-S(O)$_2$—NR$^A$—, heteroaryl-S(O)$_2$—NR$^A$—, and heterocyclyl-S(O)$_2$—NR$^A$—, where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR$^A$—, alkylO—S(O)—NR$^A$—, cycloalkylO—S(O)—NR$^A$—, arylO—S(O)—NR$^A$—, heteroarylO—S(O)—NR$^A$—, and heterocyclylO—S(O)—NR$^A$—, where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR$^A$—, alkylO—S(O)$_2$—NR$^A$—, cycloalkylO—S(O)$_2$—NR$^A$—, arylO—S(O)$_2$—NR$^A$—, heteroarylO-S(O)$_2$—NR$^A$—, and heterocyclylO—S(O)$_2$—NR$^A$—, where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R$^A$R$^A$N—C(S)—, where each R$^A$ is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR$^A$—, alkyl-C(S)—NR$^A$—, cycloalkyl-C(S)—NR$^A$—, aryl-C(S)—NR$^A$—, heteroaryl-C(S)—NR$^A$—, and heterocyclyl-C(S)—NR$^A$—, where R$^A$ is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R$^A$R$^A$N—S(O)—, where each R$^A$ is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R$^A$R$^A$N—S(O)$_2$—, where each R$^A$ is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

In an embodiment the "optionally substituted" group is selected from halo (e.g., chloro, fluoro or bromo), —CN, —NO$_2$, —CO$_2$H, —CO$_2$C$_{1-6}$alkyl, —CONH$_2$, —CONH(C$_{1-6}$alkyl), —CONH(C$_{1-6}$alkyl)$_2$, —OH, hydroxyC$_{1-6}$alkyl, C$_{1-6}$alkoxy, C$_{1-6}$alkyl, C$_{1-6}$acyl, carboxyC$_{1-6}$alkyl, acetyl, trifluoromethyl, benzyloxy, phenyl, phenoxy, —NH$_2$, —NH(C$_{1-6}$alkyl) or —N(C$_{1-6}$alkyl)$_2$.

As described generally above, the present invention provides compounds of formula (I) and salts thereof,

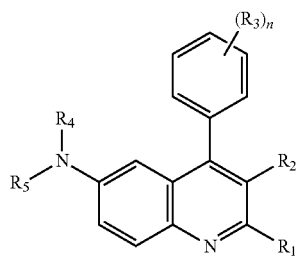

(I)

wherein $R_1$, $R_2$, $R_3$, $R_4$, $R_5$, and n are as described herein.

In certain embodiments, the present invention provides a compound of formula (Ia):

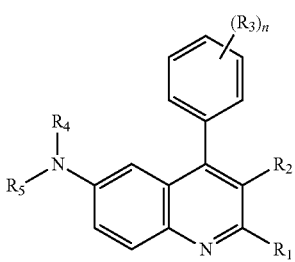

(Ia)

wherein $R_1$ represents $C_1$-$C_4$ alkyl;

$R_2$ represents —C(O)NR'R" (where R' is H or $C_1$-$C_4$ alkyl and R" is $C_1$-$C_4$ alkyl, OH or CN), —C(O)OR' (where R' is H or $C_1$-$C_4$ alkyl), —C(O)NHSO$_2$R''' (where R''' is aryl or $C_1$-$C_3$ alkyl), —S(O)$_2$NHR'''' (where R'''' is H, $C_1$-$C_3$ alkyl, or aryl), optionally substituted heteroaryl or optionally substituted heterocyclyl;

$R_3$ represents carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, or optionally substituted thioacylamino;

$R_4$ represents H, optionally substituted alkyl, optionally substituted aryl, optionally substituted cycloalkyl, optionally substituted acyl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl;

$R_5$ represents optionally substituted cycloalkyl or optionally substituted cycloalkenyl; and n is 0 or an integer of 1 to 4.

In some embodiments, $R_1$ is $C_1$-$C_4$ alkyl. In some embodiments, $R_1$ is methyl, ethyl, isopropyl, n-propyl, or butyl. In certain embodiments, $R_1$ is $C_1$-$C_2$ alkyl. In certain embodiments, $R_1$ is methyl. In certain embodiments, $R_1$ is ethyl.

In certain embodiments, $R_2$ represents —C(O)NR'R" (where R' is —H or optionally substituted $C_1$-$C_6$ alkyl and R" is optionally substituted $C_1$-$C_6$ alkyl, —OH or —CN, or R' and R" together form an optionally substituted heterocyclyl), —C(O)OH, —C(O)NHSO$_2$R''' (where R''' is optionally substituted aryl or optionally substituted $C_1$-$C_6$ alkyl), —S(O)$_2$NHR'''' (where R'''' is —H, optionally substituted $C_1$-$C_6$ alkyl, or optionally substituted aryl), optionally substituted heteroaryl or optionally substituted heterocyclyl.

In some embodiments, $R_2$ is —C(O)NR'R", wherein R' is H or $C_1$-$C_4$ alkyl, and R" is $C_1$-$C_4$ alkyl, —OH, or —CN. In certain embodiments, $R_2$ is —C(O)NR'R", wherein R' is H and R" is —OH or —CN. In certain embodiments, $R_2$ is —C(O)NHOH. In certain embodiments, $R_2$ is —C(O)NHCN. In certain embodiments, $R_2$ is —C(O)NH($C_1$-$C_4$ alkyl). In certain embodiments, $R_2$ is —C(O)NHMe or —C(O)NHEt.

In some embodiments, $R_2$ is —C(O)NR'R", wherein R' and R" taken together form an optionally substituted heterocyclyl. In certain embodiments, R' and R" taken together form a 5-7 membered heterocyclyl having 1-2 heteroatoms selected from nitrogen, oxygen, and sulfur. In certain embodiments, R' and R" taken together form a 5-membered heterocyclyl having 1-2 heteroatoms selected from nitrogen, oxygen, and sulfur. In certain embodiments, R' and R" taken together form a 6-membered heterocyclyl having 1-2 heteroatoms selected from nitrogen, oxygen, and sulfur. In certain embodiments, R' and R" taken together form a 5-membered heterocyclyl having one heteroatom selected from nitrogen, oxygen, and sulfur. In certain embodiments, R' and R" taken together form a 6-membered heterocyclyl having one heteroatom selected from nitrogen, oxygen, and sulfur. In certain embodiments, R' and R" taken together form a 6-membered heterocyclyl having two heteroatoms selected from nitrogen, oxygen, and sulfur. In certain embodiments, R' and R" taken together form a morpholine ring.

In certain embodiments, $R_2$ is —C(O)OR', wherein R' is hydrogen or optionally substituted $C_1$-$C_6$ alkyl. In certain embodiments, $R_2$ is —C(O)OR', wherein R' is $C_1$-$C_3$ alkyl. In certain embodiments, $R_2$ is —CO$_2$Me or —CO$_2$Et.

In certain embodiments, $R_2$ is —C(O)OH.

In some embodiments, $R_2$ is —C(O)NHSO$_2$R''', wherein R''' is aryl or $C_1$-$C_3$ alkyl. In certain embodiments, $R_2$ is —C(O)NHSO$_2$(phenyl). In certain embodiments, $R_2$ is —C(O)NHSO$_2$($C_1$-$C_3$ alkyl). In certain embodiments, $R_2$ is —C(O)NHSO$_2$Me, —C(O)NHSO$_2$Et, or —C(O)NHSO$_2$iPr.

In some embodiments, $R_2$ is —S(O)$_2$NHR'''', wherein R'''' is H, $C_1$-$C_3$ alkyl, or aryl. In certain embodiments, $R_2$ is —S(O)$_2$NH$_2$. In certain embodiments, $R_2$ is —S(O)$_2$NH($C_1$-$C_3$ alkyl). In certain embodiments, $R_2$ is —S(O)$_2$NHMe, —S(O)$_2$NHEt, or —S(O)$_2$NHiPr. In certain embodiments, $R_2$ is —S(O)$_2$NH(aryl).

In some embodiments, $R_2$ is optionally substituted heteroaryl or optionally substituted heterocyclyl. In some embodiments, $R_2$ is substituted or unsubstituted 5-6 membered heteroaryl having 1-3 heteroatoms selected from nitrogen, oxygen, and sulfur. In some embodiments, $R_2$ is a substituted or unsubstituted 5-membered heteroaryl having 1-3 heteroatoms selected from nitrogen, oxygen, and sulfur. In certain embodiments, $R_2$ is a substituted or unsubstituted 6-membered heteroaryl having 1-3 nitrogens. In some embodiments, $R_2$ is a substituted or unsubstituted 4-7 membered heterocycle having 1-3 heteroatoms selected from nitrogen, oxygen, and sulfur. In certain embodiments, $R_2$ is a substituted or unsubstituted 4-membered heterocycle having one heteroatom selected from nitrogen, oxygen, and sulfur. In certain embodiments, $R_2$ is a substituted or unsubstituted 5-membered heterocycle having one heteroatom selected from nitrogen, oxygen, and sulfur. In certain embodiments, $R_2$ is a substituted or unsubstituted 6-membered heterocycle having 1-2 heteroatoms selected from nitrogen, oxygen, and sulfur. In certain embodiments, $R_2$ is a substituted or unsubstituted 7-membered heterocycle having 1-2 heteroatoms selected from nitrogen, oxygen, and sulfur. In certain embodiments, $R_2$ is one of the following:

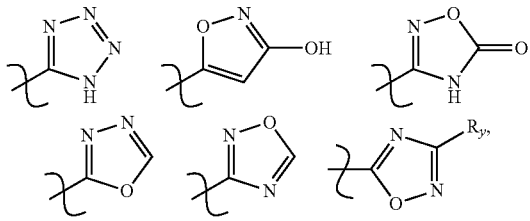

where $R_y$ is H or $C_{1-6}$ alkyl.

In some embodiments, n is 0. In other embodiments, n is an integer from 1 to 4, inclusive. In certain embodiments, n is 1. In certain embodiments, n is 2. In certain embodiments, n is 3. In certain embodiments, n is 4.

In the above embodiments $R_3$, when present, includes the following groups:

In some embodiments, $R_3$ is halogen, cyano, nitro, or amino. In certain embodiments, $R_3$ is bromo or chloro. In some embodiments, $R_3$ is fluoro.

In some embodiments, $R_3$ is an optionally substituted alkyl group. In certain embodiments, $R_3$ is an unsubstituted alkyl group. In certain embodiments, $R_3$ is a substituted alkyl group. In certain embodiments, $R_3$ is optionally substituted $C_1$-$C_6$ alkyl. In certain embodiments, $R_3$ is optionally substituted $C_1$-$C_3$ alkyl. In certain embodiments, $R_3$ is methyl or ethyl. In certain embodiments, $R_3$ is 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, or 2-nitroethyl. In certain embodiments, $R_3$ is trihalomethyl. In certain embodiments, $R_3$ is trifluoromethyl. In certain embodiments, $R_3$ is pentahaloethyl.

In some embodiments, $R_3$ is an optionally substituted aryl group. In certain embodiments, $R_3$ is unsubstituted aryl. In certain embodiments, $R_3$ is phenyl or napthyl. In certain embodiments, $R_3$ is substituted aryl. In certain embodiments, $R_3$ is halophenyl (for instance, fluorophenyl), aminophenyl, carboxyphenyl, hydroxyphenyl, cyanophenyl, nitrophenyl, trihaloalkylphenyl, or alkylphenyl.

In some embodiments, $R_3$ is an optionally substituted acyl group. In certain embodiments, $R_3$ is unsubstituted acyl. In certain embodiments, $R_3$ is substituted acyl. In certain embodiments, $R_3$ is formyl, acetyl, propionyl, or benzoyl. In certain embodiments, $R_3$ is formyl, acetyl, propionyl, or benzoyl, optionally substituted with methyl, methoxy, halogen, nitro, trifluoromethyl or cyano.

In some embodiments, $R_3$ is a substituted or unsubstituted alkoxy group. In certain embodiments, $R_3$ is $C_1$-$C_6$ alkoxy. In certain embodiments, $R_3$ is $C_1$-$C_3$ alkoxy. In certain embodiments, $R_3$ is methoxy or ethoxy. In certain embodiments, $R_3$ is dihalomethoxy. In certain embodiments, $R_3$ is trihalomethoxy. In certain embodiments, $R_3$ is trifluoromethoxy.

In some embodiments, $R_3$ is a substituted or unsubstituted oxyacyl group. In certain embodiments, $R_3$ is $C_1$-$C_6$ alkoxycarbonyl. In certain embodiments, $R_3$ is methoxycarbonyl, ethoxycarbonyl, propoxycarbonyl, butyloxycarbonyl, or isobutyloxycarbonyl.

In some embodiments, $R_3$ is a substituted or unsubstituted acyloxy group. In certain embodiments, $R_3$ is $C_1$-$C_6$ acyloxy. In certain embodiments, $R_3$ is acetoxy or propioxy.

In some embodiments, $R_3$ is an optionally substituted arylalkyl group. In certain embodiments, $R_3$ is an unsubstituted arylalkyl group. In certain embodiments, $R_3$ is benzyl. In certain embodiments, $R_3$ is a substituted arylalkyl group. In certain embodiments, $R_3$ is 1-hydroxybenzyl or 1-thiobenzyl.

In some embodiments, $R_3$ is an optionally substituted sulfinyl group. In certain embodiments, $R_3$ is alkylsulfinyl or arylsulfinyl. In certain embodiments, $R_3$ is alkoxysulfinyl. In certain embodiments, $R_3$ is methylsulfinyl, ethylsulfinyl, benzene sulfinyl, methoxysulfinyl, or ethoxysulfinyl. In certain embodiments, $R_3$ is benzene sulfinyl, optionally substituted with methyl, methoxy, halogen, nitro, trifluoromethane or cyano.

In some embodiments, $R_3$ is an optionally substituted sulfonyl group. In certain embodiments, $R_3$ is alkylsulfonyl or arylsulfonyl. In certain embodiments, $R_3$ is methylsulfonyl, ethylsulfonyl, or benzenesulfonyl (optionally substituted with methyl, methoxy, halogen, nitro, trifluoromethane or cyano).

In some embodiments, $R_3$ is an optionally substituted oxyacylamino group. In certain embodiments, $R_3$ is $C_1$-$C_6$ alkoxycarbonylamido. In certain embodiments, $R_3$ is methoxycarbonylamido or ethoxycarbonylamido.

In some embodiments, $R_3$ is an optionally substituted oxythioacyl group. In certain embodiments, $R_3$ is $C_1$-$C_6$ alkoxythiocarbonyl. In certain embodiments, $R_3$ is methoxythiocarbonyl or ethoxythiocarbonyl. In some embodiments, $R_3$ is an optionally substituted thioacyloxy group. In certain embodiments, $R_3$ is thionoacetoxy or thionopropionoxy.

In some embodiments, $R_3$ is an optionally substituted sulphinylamino group. In certain embodiments, $R_3$ is alkylsulfinylamino or arylsulfinylamino. In certain embodiments, $R_3$ is methylsulfinylamino, ethylsulfinylamino, or benzenesulfinylamino. In certain embodiments, $R_3$ is benzenesulfinylamino optionally substituted with methyl, methoxy, halogen, nitro, trifluoromethane or cyano.

In some embodiments, $R_3$ is an amino group. In certain embodiments, $R_3$ is alkylamino or dialkylamino. In certain embodiments, $R_3$ is N-methylamino or N,N'-dimethylamino. In certain embodiments, $R_3$ is a substituted amino group, such as a residue of L-valine, D-valine, L-alanine, D-alanine, aspartic acid, or alanylserine.

In certain embodiments, $R_3$ is an optionally substituted sulphonylamino group. In certain embodiments, $R_3$ is alkylsulfonylamino or arylsulfonylamino. In certain embodiments, $R_3$ is $C_1$-$C_6$ alkylsulfonylamino. In certain embodiments, $R_3$ is methylsulfonylamino, ethylsulfonylamino or benzenesulfonylamino. In certain embodiments, $R_3$ is benzenesulfonylamino optionally substituted with methyl, methoxy, halogen, nitro, trifluoromethane or cyano.

In some embodiments, $R_3$ is an optionally substituted thio group. In certain embodiments, $R_3$ is a substituted thio group. In certain embodiments, $R_3$ is alkylthio. In certain embodiments, $R_3$ is $C_1$-$C_6$ alkylthio. In certain embodiments, $R_3$ is thiomethyl or thioethyl. In certain embodiments, $R_3$ is trihalomethanethio.

In some embodiments, $R_3$ is an optionally substituted oxysulfinylamino group. In certain embodiments, $R_3$ is alkoxysulfinylamino. In certain embodiments, $R_3$ is methoxysulfinylamino or ethoxysulfinylamino.

In some embodiments, $R_3$ is an optionally substituted oxysulfonylamino group. In certain embodiments, $R_3$ is alkoxylsulfonylamino. In certain embodiments, $R_3$ is methoxysulfonylamino or ethoxysulfonylamino.

In some embodiments, $R_3$ is an optionally substituted alkenyl group. In some embodiments, $R_3$ is unsubstituted alkenyl. In some embodiments, $R_3$ is substituted alkenyl. In certain embodiments, $R_3$ is 1-propenyl, vinyl, nitrovinyl, cyano vinyl, or trifluorovinyl or styryl. In certain embodiments $R_3$ is styryl optionally substituted with methyl, methoxy, halogen, nitro, trifluoromethane or cyano. In certain embodiments, $R_3$ is trihaloethenyl.

In some embodiments, $R_3$ is an optionally substituted alkynyl group. In some embodiments, $R_3$ is substituted $C_1$-$C_6$ alkynyl. In some embodiments, $R_3$ is unsubstituted $C_1$-$C_6$ alkynyl. In certain embodiments, $R_3$ is 1-propynyl, ethynyl or trimethylsilylethynyl.

In certain embodiments, n is 1 and $R_3$ is selected from halogen, —CN, —$CF_3$, amino, hydroxyl, —$NHC_1$-$C_3$ alkyl, —$N(C_1$-$C_3$ alkyl$)_2$, —COOH, —COO($C_1$-$C_3$ alkyl), phenyl, benzyl, $C_1$-$C_3$ alkyl or $C_1$-$C_3$ alkoxy.

In certain embodiments, n is 2 and each $R_3$ is independently selected from halogen, —CN, —$CF_3$, amino, hydroxyl, —$NHC_1$-$C_3$ alkyl, —$N(C_1$-$C_3$ alkyl$)_2$, —COOH, —COO($C_1$-$C_3$ alkyl), phenyl, benzyl, $C_1$-$C_3$ alkyl or $C_1$-$C_3$ alkoxy.

In certain embodiments, n is 3 and each $R_3$ is independently selected from halogen, —CN, —$CF_3$, amino, hydroxyl, —$NHC_1$-$C_3$ alkyl, —$N(C_1$-$C_3$ alkyl$)_2$, —COOH, —COO($C_1$-$C_3$ alkyl), phenyl, benzyl, $C_1$-$C_3$ alkyl or $C_1$-$C_3$ alkoxy.

In certain embodiments, $R_4$ is $C_1$-$C_3$ alkyl or H. In certain embodiments, $R_4$ is H. In certain embodiments, $R_4$ is methyl, ethyl, n-propyl, or isopropyl.

In certain embodiments, $R_2$ is —COOH, and $R_4$ is H.

In certain embodiments, $R_5$ is a benzofused $C_5$-$C_7$ cycloalkyl (wherein the benzene ring may be optionally substituted). In certain embodiments, $R_5$ is an optionally substituted indanyl or optionally substituted 1,2,3,4-tetrahydronaphthalenyl. In certain embodiments, $R_5$ is unsubstituted indanyl or 1,2,3,4-tetrahydronaphthalenyl. In certain embodiments, $R_5$ is an optionally substituted benzofused $C_5$-$C_7$ cycloalkyl, such as indanyl or 1,2,3,4-tetrahydronaphthalenyl, wherein the optional substitutents are independently selected from the group consisting of halo (e.g., chloro, fluoro or bromo), —CN, —$NO_2$, —$CO_2H$, —$CO_2C_{1-6}$alkyl, —$CONH_2$, —CONH($C_{1-6}$alkyl), —CONH($C_{1-6}$alkyl$)_2$, —OH, hydroxyalkyl, alkoxy, alkyl, acyl, carboxyalkyl, acetyl, trifluoromethyl, benzyloxy, phenoxy, —$NH_2$, —NH($C_{1-6}$alkyl) or —N($C_{1-6}$alkyl$)_2$.

In certain embodiments, $R_5$ is:

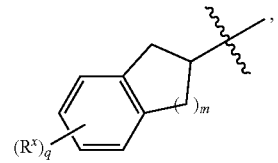

wherein m is 1, 2, or 3; q is 1, 2, 3, or 4; and $R^x$ is halo (e.g., chloro, fluoro or bromo), —CN, —$NO_2$, —$CO_2H$, —$CO_2$ $C_{1-6}$alkyl, —$CONH_2$, —CONH($C_{1-6}$alkyl), —CONH($C_{1-6}$alkyl$)_2$, —OH, hydroxyalkyl, alkoxy, alkyl, acyl, carboxyalkyl, acetyl, trifluoromethyl, benzyloxy, phenoxy, —$NH_2$, —NH($C_{1-6}$alkyl) or —N($C_{1-6}$alkyl$)_2$.

In some embodiments, m is 1. In some embodiments, m is 2. In some embodiments, m is 3. In some embodiments, q is 1. In some embodiments, q is 2. In some embodiments, q is 3. In some embodiments, q is 4. In certain embodiments, m is 1 and q is 1.

In certain embodiments, $R_5$ is:

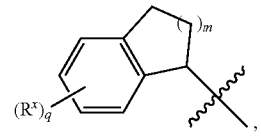

wherein m is 1, 2, or 3; q is 1, 2, 3, or 4; and $R^x$ is halo (e.g., chloro, fluoro or bromo), —CN, —$NO_2$, —$CO_2H$, —$CO_2$ $C_{1-6}$alkyl, —$CONH_2$, —CONH($C_{1-6}$alkyl), —CONH($C_{1-6}$alkyl$)_2$, —OH, hydroxyalkyl, alkoxy, alkyl, acyl, carboxyalkyl, acetyl, trifluoromethyl, benzyloxy, phenoxy, —$NH_2$, —NH($C_{1-6}$alkyl) or —N($C_{1-6}$alkyl$)_2$.

In certain embodiments, $R_5$ is:

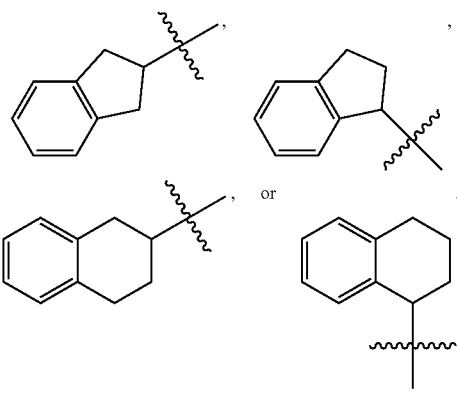

In certain embodiments, $R_5$ is a benzofused $C_5$-$C_7$ cycloalkenyl (wherein the benzene ring may be optionally substituted). In certain embodiments, $R_5$ is optionally substituted indenyl. In certain embodiments, $R_5$ is unsubstituted indenyl.

In certain embodiments, $R_4$ is hydrogen, and $R_5$ is a benzofused $C_5$-$C_7$ cycloalkyl. In certain embodiments, $R_4$ is $C_1$-$C_3$ alkyl, and $R_5$ is a benzofused $C_5$-$C_7$ cycloalkyl. In certain embodiments, $R_4$ is hydrogen, and $R_5$ is a benzofused $C_5$-$C_7$ cycloalkenyl. In certain embodiments, $R_4$ is $C_1$-$C_3$ alkyl, and $R_5$ is a benzofused $C_5$-$C_7$ cycloalkenyl. In certain embodiments, $R_4$ is hydrogen, and $R_5$ is indanyl. In certain embodiments, $R_4$ is methyl, and $R_5$ is indanyl. In certain embodiments, $R_4$ is hydrogen, and $R_5$ is indenyl. In certain embodiments, $R_4$ is methyl, and $R_5$ is indenyl. In certain embodiments, $R_4$ is hydrogen, and $R_5$ is 1,2,3,4-tetrahydronaphthalenyl. In certain embodiments, $R_4$ is methyl, and $R_5$ is 1,2,3,4-tetrahydronaphthalenyl.

In certain embodiments, the invention provides compounds of formula (Ib) or salts thereof:

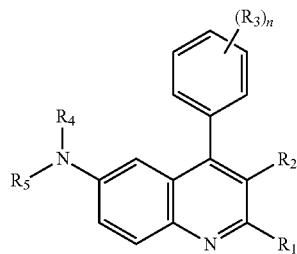

(Ib)

wherein
n is 0 or 1;
$R_1$ is $C_1$-$C_2$ alkyl;
$R_2$ is —COOH or —C(O)NR'R" (where R' and R" together form an optionally substituted morpholinyl);
$R_3$, when present, is selected from the group consisting of halogen, —CN, —$CF_3$, amino, hydroxyl, —$NHC_1$-$C_3$ alkyl, —$N(C_1$-$C_3$ alkyl$)_2$, —COOH, —COO($C_1$-$C_3$ alkyl), phenyl, benzyl, $C_1$-$C_3$ alkyl or $C_1$-$C_3$ alkoxy;
$R_4$ is H or $C_1$-$C_3$ alkyl; and
$R_5$ is an optionally substituted benzofused $C_5$-$C_7$ cycloalkyl.

With reference to formula (Ib), in some embodiments, one or more of the following definitions apply:
(a) n is 0,
(b) $R_1$ is methyl,
(c) $R_2$ is —COOH,
(d) $R_4$ is H,
(e) $R_5$ is indanyl or 1,2,3,4-tetrahydronaphthalenyl, optionally substituted 1 or 2 times by halo (e.g., chloro, fluoro or bromo), —CN, —$NO_2$, —$CO_2H$, —$CO_2C_{1-6}$alkyl, —$CONH_2$, —$CONH(C_{1-6}$alkyl), —$CON(C_{1-6}$alkyl$)_2$, —OH, hydroxyalkyl, alkoxy, alkyl, acyl, carboxyalkyl, acetyl, trifluoromethyl, benzyloxy, phenoxy, —$NH_2$, —$NH(C_{1-6}$alkyl) or —$N(C_{1-6}$alkyl$)_2$.

In certain embodiments, the invention provides compounds of formula (Ic) or salts thereof:

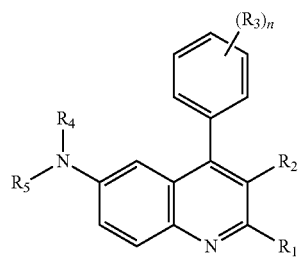

(Ic)

wherein
n is 0 or 1;
$R_1$ is $C_1$-$C_2$ alkyl;
$R_2$ is —COOR' (where R' is H or $C_1$-$C_4$ alkyl);
$R_3$, when present, is selected from the group consisting of halogen, —CN, —$CF_3$, amino, hydroxyl, —$NHC_1$-$C_3$ alkyl, —$N(C_1$-$C_3$ alkyl$)_2$, —COOH, —COO($C_1$-$C_3$ alkyl), phenyl, benzyl, $C_1$-$C_3$ alkyl or $C_1$-$C_3$ alkoxy;
$R_4$ is H or $C_1$-$C_3$ alkyl; and
$R_5$ is an optionally substituted benzofused $C_5$-$C_7$ cycloalkyl.

In certain embodiments, the invention provides compounds of formula (I), (Ia), (Ib), or (Ic) or salts thereof, wherein $R_1$ is methyl, $R_2$ is —COOH, $R_4$ is H and $R_5$ is indanyl or 1,2,3,4-tetrahydronaphthalenyl.

In certain embodiments, the invention provides compounds of formula (I), (Ia) or (Ib) or salts thereof, wherein $R_1$ is methyl, $R_2$ is —C(O)morpholinyl, $R_4$ is H and $R_5$ is indanyl or 1,2,3,4-tetrahydronaphthalenyl.

For compounds of formula (I), (Ia), (Ib), or (Ic), in certain embodiments, $R_5$ is optionally substituted indanyl. In certain embodiments, $R_5$ is indanyl.

Representative compounds of the present invention include:

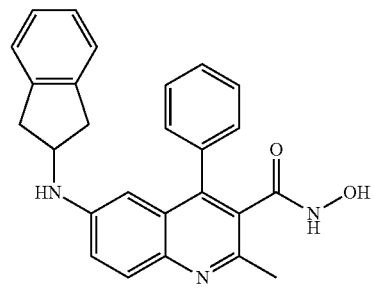

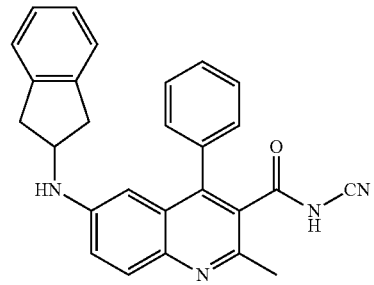

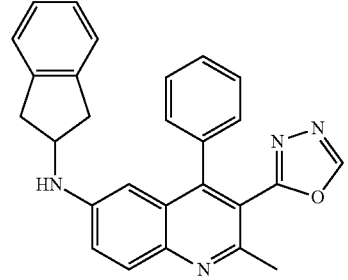

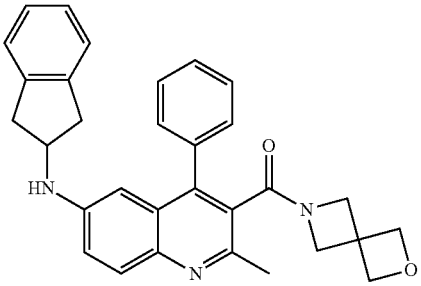

17
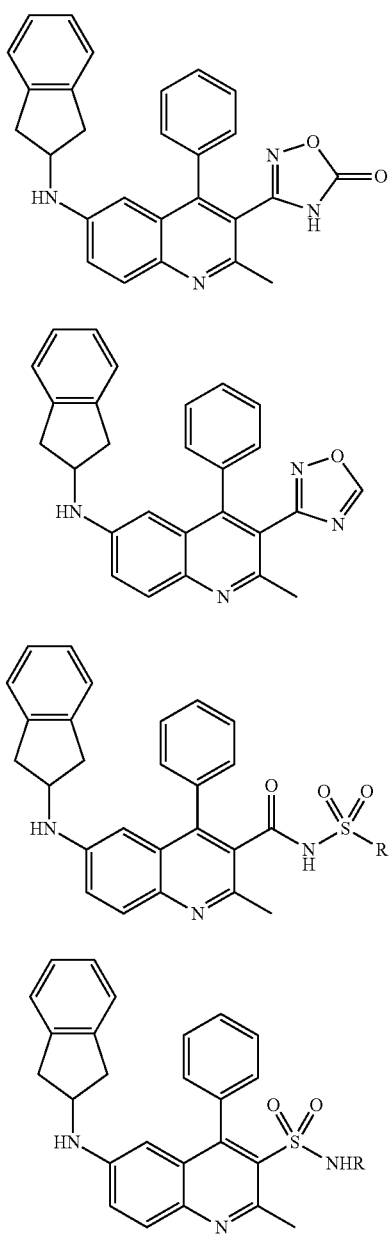
18
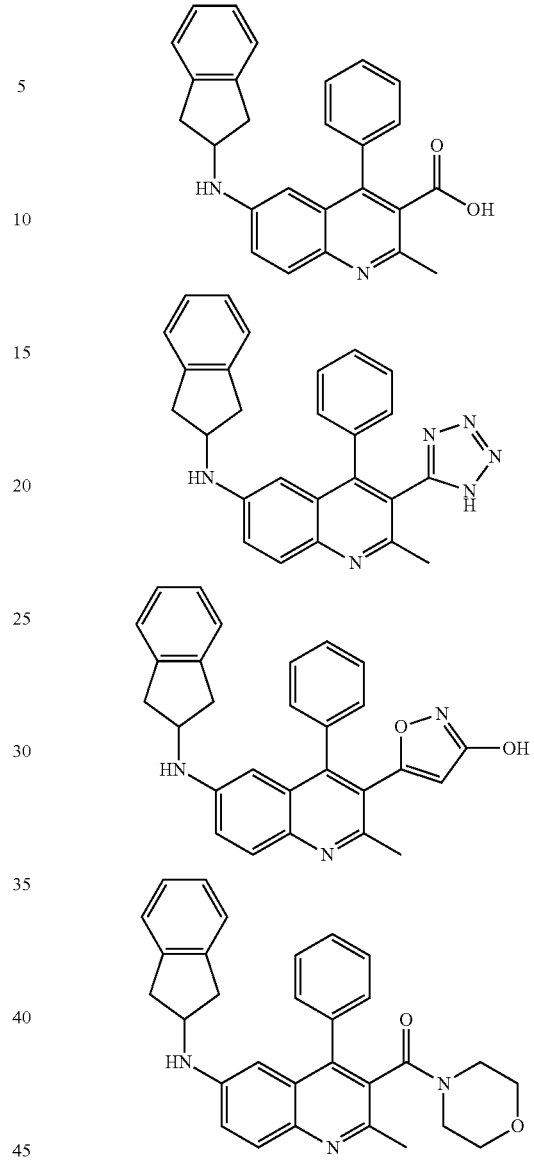
In certain embodiments, R is H, aryl, or $C_{1-3}$ alkyl.
The compounds of the present invention can be prepared according to Schemes 1 to 6 below:
Scheme 1
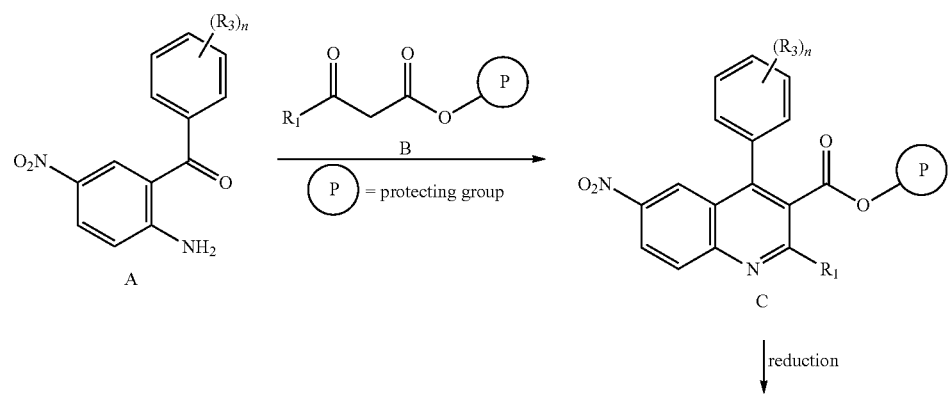
reduction

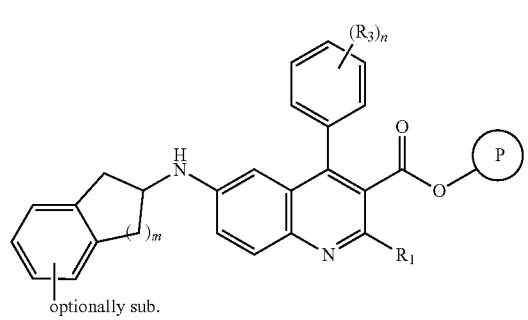
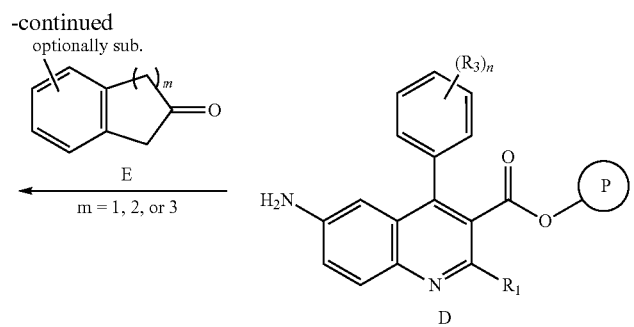
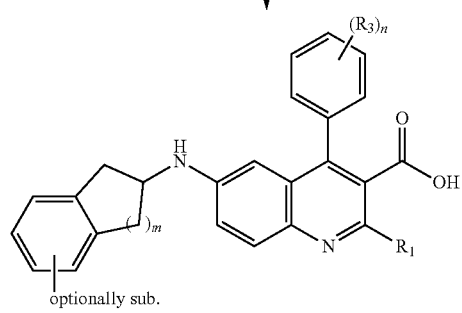
Compounds of formula G of the invention may be prepared by initially reacting a 2-amino-5-nitrobenzophenone of formula A with a protected acetoacetate of formula B to afford the quinoline C. Reduction of the nitro group may afford D which can subsequently be coupled to ketone of formula E to prepare compounds of formula F. Deprotection of F may afford the acid G.
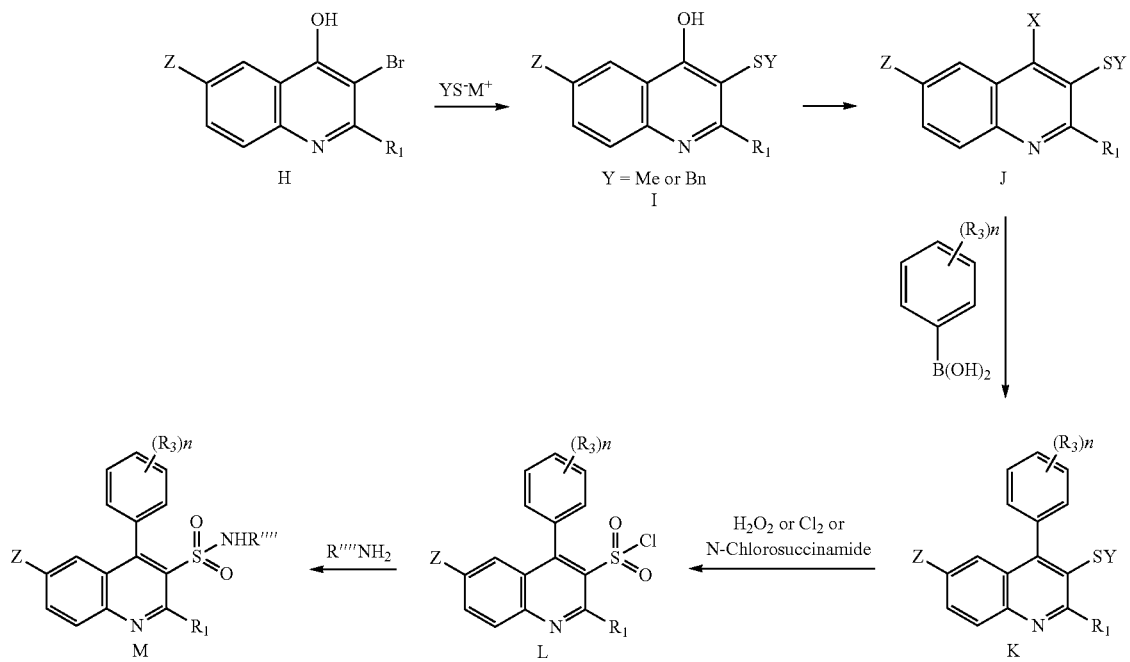

According to scheme 2,3-bromo-quinolin-4-ol derivatives of formula H (Z=NR₄R₅ or NO₂) can be reacted with alkali- (e.g. sodium metal) or alkaline-earth metal salts of methyl or benzyl thiol to provide compounds of formula I (e.g. Bioorg. Med. Chem. Lett., 2001, 9, 1141; Heterocycles 2007, 71, 1975). 3-Bromo-quinolin-4-ol derivatives of formula H are known (e.g. 3-bromo-6-(N,N'-dimethylamino)-2-(trifluoromethyl)-quinolin-4-ol: J. Chem. Info. Comp. Sci. 2001, 41, 1316) or can be synthesized from commercially available 3-bromo-quinolin-4-ol by conventional methods such as nitration with nitric acid. Conversion of compounds of formula I to J can be achieved by known halogenation methods with suitable halogenating regents (e.g. POCl₃, SOCl₂, PCl₅ and PBr₃). Compounds of formula K can be achieved by reacting compounds of formula J with aryl boronic acids according to Suzuki coupling conditions or any modification of Suzuki coupling conditions. Conversion of 4-aryl-3-sulfide-quinoline derivative of formula K to L can be achieved by known oxidative methods (e.g. Heterocycles, 1994, 38, 1317; Heterocycles 2007, 71, 1975). 3-Sulfonylchloride derivative of quinoline of formula L can be reacted suitable amino compound to provide a compound of formula M. For compound of formula M where Z=NO₂, the nitro group can be reduced to amino by known methods followed by reductive amination with suitable carbonyl compound (e.g. 2-indanone: scheme 6).

able ester of chloroformic acid (e.g. Methyl ester: J. Med. Chem., 2001, 44, 1560; phenyl ester: WO2007039172) to form a compound of formula P. The nitro group of compounds of the formula N and P can be reduced to amino by known methods, followed by reductive amination with suitable carbonyl compound (e.g. 2-indanone: scheme 6).

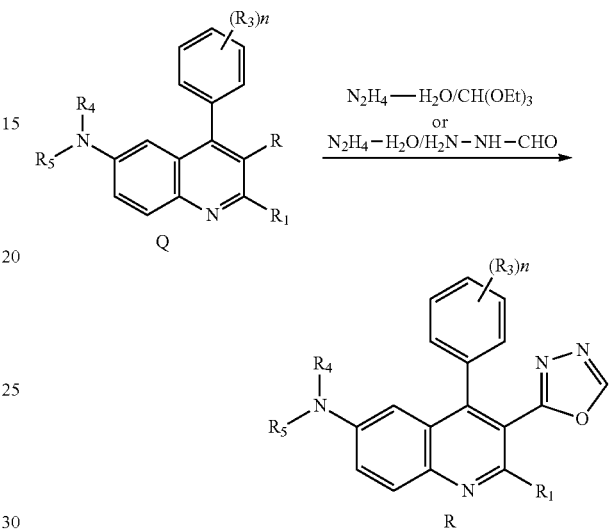

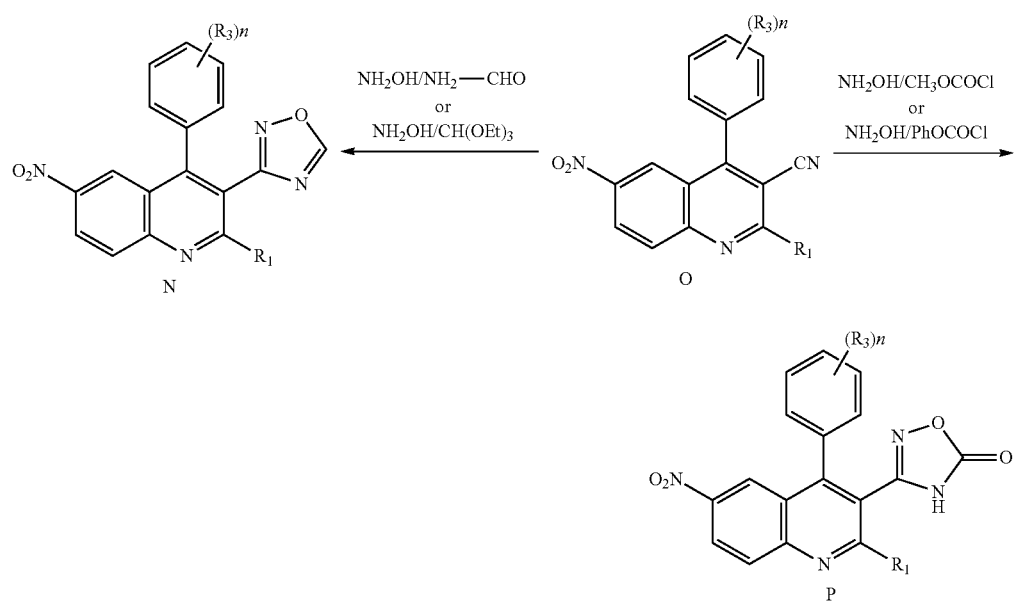

According to Scheme 3,3-(1,2,4-oxadiazole)-quinoline derivative of formula N can be synthesized by reacting 3-cyano-quinoline derivative of formula O (prepared according to scheme 6) with hydroxylamine and formamide (e.g. J. Org. Chem., 1979, 44, 1695) or hydroxylamine and triethyl orthoformate (e.g. WO200597750). 3-cyano-quinoline derivative of formula O can be reacted with hydroxylamine and a suitable ester of chloroformic acid As shown in Scheme 4,3-(1,3,4-oxadiazole)-quinoline derivative of formula R can be achieved by reacting a suitable acid (R=COOH) or ester (R=COOMe) of formula Q with hydrazine-hydrate and triethyl orthoformate (e.g. WO2010135360) or with hydrazine-hydrate and hydrazide of formic acid (e.g. Tetrahedron Letters, 2009, 65, 9989).

Scheme 5

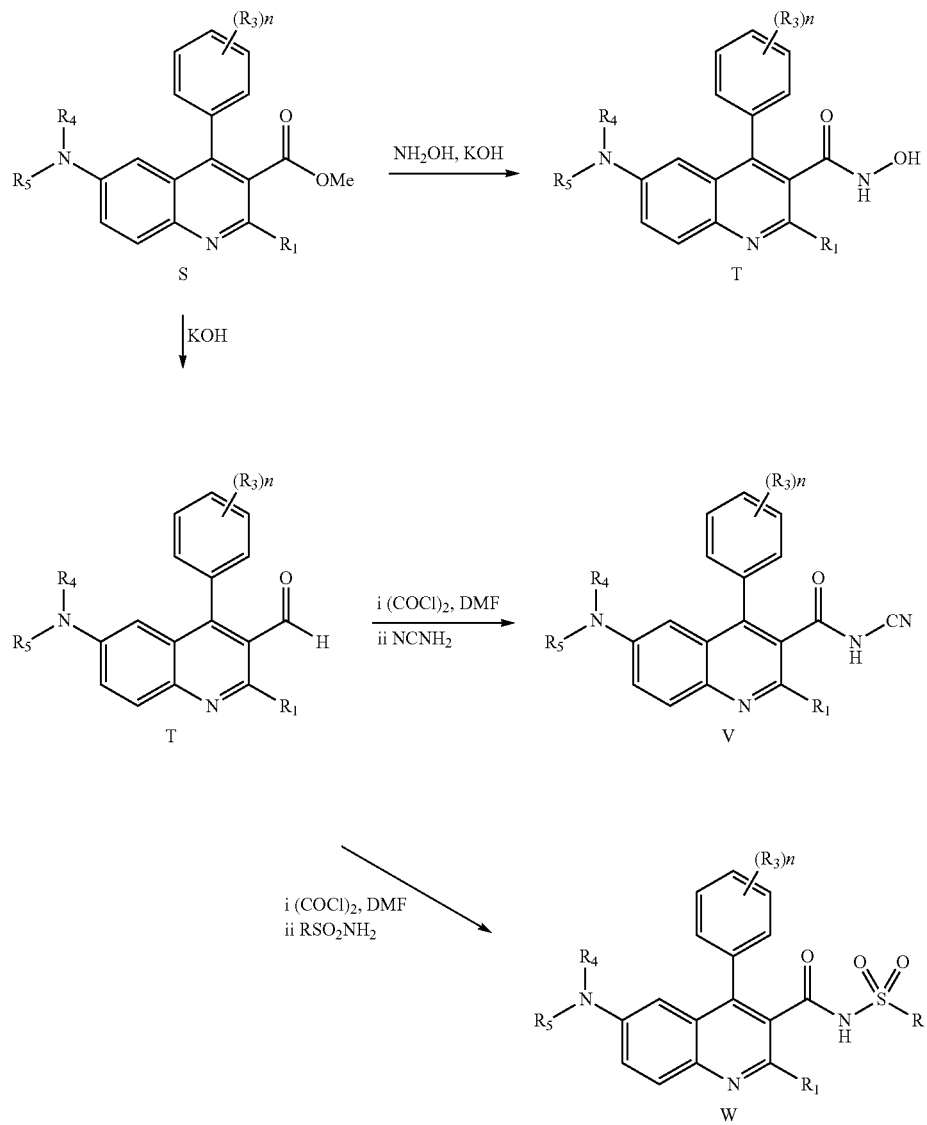

As shown in Scheme 5, compounds of the formula T can be prepared by reacting esters of formula S with hydroxylamine and potassium hydroxide. Compounds of the formula V can be prepared by converting compounds U to the corresponding acid chloride, for example with oxalyl chloride and dimethylformamide, then by treatment with cyanoamide ($NCNH_2$). Compounds of the formula W can be formed by treating these acid chlorides with a primary sulphonamide.

Scheme 6
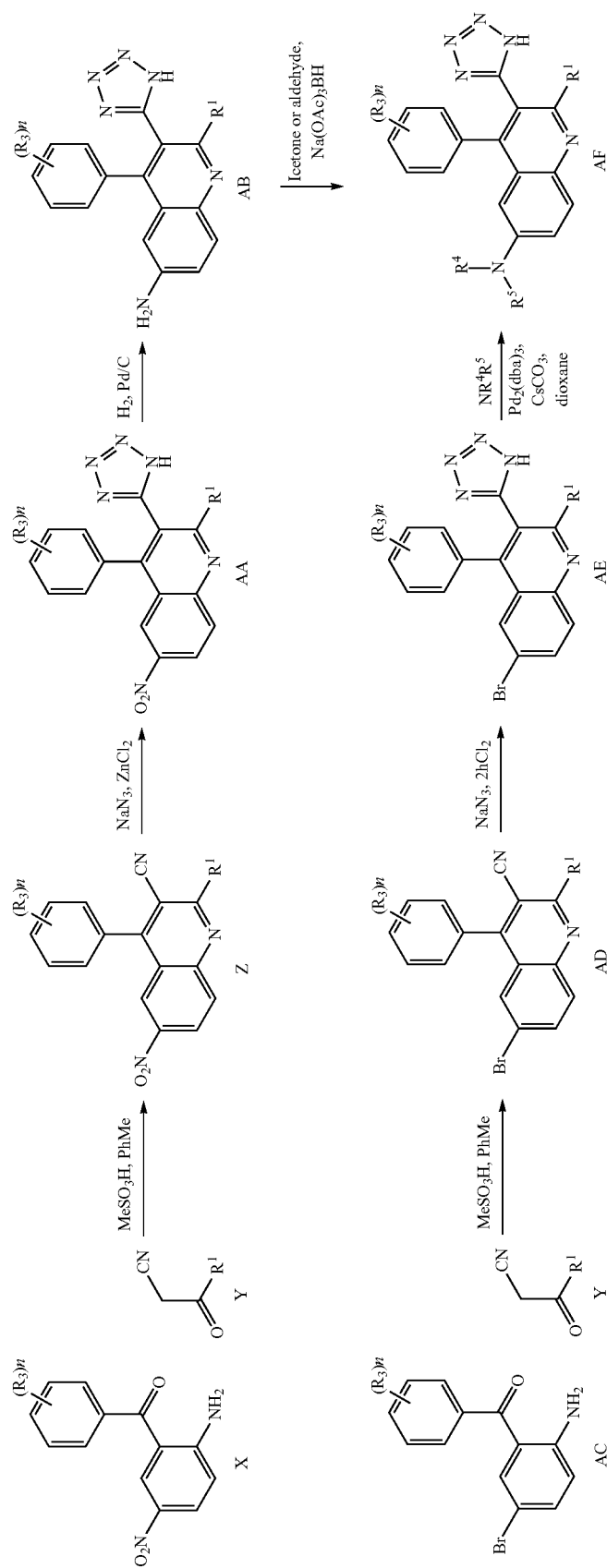

Compounds of the formula AF can be prepared by the route shown in Scheme 6 (e.g. Bioorg. Med. Chem. Lett. 2011, 19 (15) 4482). Reaction of 2-aminobenzophenones X or AC with alpha-cyanoketones can form 3-cyanoquinolines Z or AD respectively. Compounds Z or AD can be reacted with sodium azide to give tetrazoles AA or AE. 6-Nitro-3-tetrazolylquinolines of the formula AA can be reduced, for example by hydrogenation, to give the 6-aminoquinolines AB Either one or two successive reductive aminations of compounds of the formula AB with aldehydes or ketones can give compounds of the formula AF. Alternatively compounds of the formula AE can undergo Buchwald coupling with amines to give compounds of the formula AF.

Other compounds of formula I can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR*R** from —CO$_2$CH$_3$ by heating with or without catalytic metal cyanide, e.g. NaCN, and HNR*R** in CH$_3$OH; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN=C=O or RN=C=O; —NRC(O)R* from —NHR by treatment with ClC(O)R* in pyridine; —C(=NR)NR*R** from —C(NR*R**)SR with H$_3$N$^+$OAc$^-$ by heating in alcohol; —C(NR*R**)SR from —C(S)NR*R** with R—I in an inert solvent, e.g. acetone; —C(S)NR*R** (where R* or R** is not hydrogen) from —C(S)NH$_2$ with HNR*R**; —C(=NCN)—NR*R** from —C(=NR*R**)—SR with NH$_2$CN by heating in anhydrous alcohol, alternatively from —C(=NH)—NR*R** by treatment with BrCN and NaOEt in EtOH; —NR—C(=NCN)SR from —NHR* by treatment with (RS)$_2$C=NCN; —NR**SO$_2$R from —NHR* by treatment with ClSO$_2$R by heating in pyridine; —NR*C(S)R from —NR*C(O)R by treatment with Lawesson's reagent [2,4-bis (4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR* with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R* from RC(O)R* by R**CO$_3$H; —CCH$_2$OH from —C(O)OR* with Na/R*OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH.

One of ordinary skill in the art will appreciate that the synthetic methods, as described herein, may necessitate a variety of protecting groups. By the term "protecting group", as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4''-tis(4,5-dichlorophthalimidophenyl) methyl, 4,4',4''-tris(levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in Protective Groups in Organic Synthesis, Third Ed. Greene, T. W. and Wuts, P. G., Eds., John Wiley & Sons, New York: 1999, the entire contents of which are hereby incorporated by reference.

Without wanting to be bound by theory it is believed that certain compounds of the present invention are not $GABA_A$ receptor agonists and their effects are mediated through biomolecules which have yet to be identified. Based on their in vivo pharmacology the compounds of the present invention may be used in the treatment of a variety of disorders of the central nervous system, including affective disorders.

Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, generalized or substance-induced anxiety disorder; neuroses; anxiety-depression mixed disorder; childhood anxiety disorders; fibromyalgia; irritable bowel syndrome; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which compounds of the invention may be of benefit include neurodegenerative disorders which occur as a result of neurodegeneration or any chronic progressive neuropathy characterized by loss of neurons in motor, sensory, or cognitive systems for example, Alzheimer's disease, Pick's disease, Lewy body dementia, Basal ganglia-Huntington's disease, Parkinson's disease, Brainstem & cerebellum-atrophy, Freidreich's ataxia, multiple system atrophy, types 1, 2, 3, 6, 7 spinocerebellar ataxia, Motor-amyotrophic lateral sclerosis, familial spastic paraparesis, spinal muscular atrophy, spinal & bulbar muscular atrophy.

Compounds of the invention may also be beneficial in enhancing cognition, for example in subjects suffering from dementing conditions such as Alzheimer's disease or mild cognitive impairment. Compounds of the invention may also be effective as pre-medication prior to anaesthesia or minor procedures such as endoscopy, including gastric endoscopy.

The invention also provides for the use of a compound of formula (I), (Ia), (Ib), or (Ic) in the manufacture of a medicament for treating disorders of the central nervous system.

There is also provided a method of treatment of disorders of the central nervous system comprising the administration of an effective amount of at least one compound of formula (I), (Ia), (Ib), or (Ic) to a subject in need thereof.

It will be understood that the compounds of the invention can be used in the treatment of anxiety or conditions/disease states associated with anxiety such as irritable bowel syndrome and fibromyalgia.

In certain embodiments, an anxiety disorder is classified as one of the following:
panic disorder,
obsessive-compulsive disorder (OCD),
post-traumatic stress disorder (PTSD),
social phobia (or social anxiety disorder—SAD),
specific phobias,
generalized anxiety disorder (GAD),
substance-induced anxiety disorder, and
acute stress disorder (ASD).

In an embodiment the compounds of the invention may be used in the treatment of a panic disorder.

In an embodiment the compounds of the invention may be used in the treatment of obsessive-compulsive disorder (OCD).

In an embodiment the compounds of the invention may be used in the treatment of post-traumatic stress disorder (PTSD).

In an embodiment the compounds of the invention may be used in the treatment of social phobia (or social anxiety disorder—SAD).

In an embodiment the compounds of the invention may be used in the treatment of specific phobias.

In an embodiment the compounds of the invention may be used in the treatment of substance-induced anxiety disorder.

In an embodiment the compounds of the invention may be used in the treatment of acute stress disorder (ASD).

In an embodiment the compounds of the invention may be used in the treatment of generalized anxiety disorder (GAD).

Generalised anxiety disorder criteria include:
(i) At least 6 months of "excessive anxiety and worry" about a variety of events and situations. Generally, "excessive" can be interpreted as more than would be expected for a particular situation or event. Most people become anxious over certain things, but the intensity of the anxiety typically corresponds to the situation.
(ii) There is significant difficulty in controlling the anxiety and worry. If someone has a very difficult struggle to regain control, relax, or cope with the anxiety and worry, then this requirement is met.
(iii) The presence for most days over the previous six months of 3 or more (only 1 for children) of the following symptoms:
  1. Feeling wound-up, tense, or restless
  2. Easily becoming fatigued or worn-out
  3. Concentration problems
  4. Irritability
  5. Significant tension in muscles
  6. Difficulty with sleep
(iv) The symptoms are not part of another mental disorder.
(v) The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.
(vi) The condition is not due to a substance or medical issue.

In certain embodiments, a subject to be treated with a compound of the present invention may be identified by one or more of the above criteria for generalized anxiety disorder.

In another embodiment the compounds of the invention may be used to treat or prevent one or more symptoms associated with an anxiety disorder.

Each anxiety disorder has different symptoms, but all the symptoms cluster around excessive, irrational fear and dread.

In another embodiment the compounds of the invention may be used in the treatment of depression, and for instance, a major depressive disorder.

Major depressive disorder criteria include:
(i) At least five of the following symptoms have been present during the same 2-week period and represent a change from previous functioning: at least one of the symptoms is either
   1) depressed mood or
   2) loss of interest or pleasure.
(ii) Depressed mood most of the day, nearly every day, as indicated either by subjective report (e.g., feels sad or empty) or observation made by others (e.g., appears tearful).
(iii) Markedly diminished interest or pleasure in all, or almost all, activities most of the day, nearly every day (as indicated either by subjective account or observation made by others).
(iv) Significant weight loss when not dieting or weight gain (e.g., a change of more than 5% of body weight in a month), or decrease or increase in appetite nearly every day.
(v) Insomnia or hypersomnia nearly every day.
(vi) Psychomotor agitation or retardation nearly every day (observable by others, not merely subjective feelings of restlessness or being slowed down).
(vii) Fatigue or loss of energy nearly every day.
(viii) Feelings of worthlessness or excessive or inappropriate guilt (which may be delusional) nearly every day (not merely self-reproach or guilt about being sick).
(ix) Diminished ability to think or concentrate, or indecisiveness, nearly every day (either by subjective account or as observed by others).
(x) Recurrent thoughts of death (not just fear of dying), recurrent suicidal ideation without a specific plan, or a suicide attempt or specific plan for committing suicide
(xi) The symptoms do not meet criteria for a mixed episode.
(xii) The symptoms cause clinically significant distress or impairment in social, occupational, or other important areas of functioning.
(xiii) The symptoms are not due to the direct physiological effects of a substance (e.g. a drug of abuse, a medication) or a general medical condition (e.g., hypothyroidism).
(xiv) The symptoms are not better accounted for by bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

The above criteria has been sourced from the American Psychiatric Association (2000). Diagnostic and Statistical Manual of Mental Disorders (4th Ed., Text Revision). Washington D.C.: American Psychiatric Association.

In certain embodiments, a subject to be treated with a compound of the present invention may be identified by one or more of the above criteria for major depressive disorder.

In another embodiment the compounds of the invention may be used to treat or prevent one or more symptoms associated with depression.

Further disorders for which compounds of the invention may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal.

In an embodiment the compounds of the invention may be used in the treatment of cerebral ischemia.

In an embodiment the compounds of the invention may be used in the treatment of disorders of the circadian rhythm.

In an embodiment the compounds of the invention may be used in the treatment of pain and nociception.

In an embodiment the compounds of the invention may be used in the treatment of Alzheimer's disease.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernable symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated. In some embodiments, a treatment effective amount is a therapeutically effective amount or a prophylactically effective amount. The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another anti-anxiety or anti-depressant medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I or a pharmaceutically acceptable salt thereof, and a second amount of an additional suitable therapeutic agent.

In certain embodiments, the compound of Formula (I), (Ia), (Ib), or (Ic) and the additional therapeutic agent are each administered in an effective amount (i.e., each in an amount which would be therapeutically effective if administered alone). In other embodiments, the compound of Formula I and the additional therapeutic agent are each administered in an amount which alone does not provide a therapeutic effect (a sub-therapeutic dose). In yet other embodiments, the compound of Formula (I), (Ia), (Ib), or (Ic) can be administered in an effective amount, while the additional therapeutic agent is administered in a sub-therapeutic dose. In still other embodiments, the compound of Formula (I), (Ia), (Ib), or (Ic) can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a compound of Formula (I), (Ia), (Ib) or (Ic) and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula (I), (Ia), (Ib) or (Ic) and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with a compound of this disclosure, either administered separately or in the same pharmaceutical composition, include, but are not limited to: muscle relaxants, anticonvulants, hypnotics, anaesthetics, analgesics, cholinergics, antidepressants, mood stabilisers or other anxiolytics, etc.

In an embodiment the second therapeutic agent is an antidepressant selected from the group consisting of monoamine oxidase inhibitors (MAOIs) (e.g., Phenelzine, Moclobemide), tricyclic antidepressants (TCAs) (e.g., Surmontil, Tofranil), tetracyclic antidepressants (TeCAs) (e.g., Remeron, Deprilept), selective serotonin reuptake inhibitors (SSRIs) (e.g., Zoloft, Prozac, Celexa) and serotonin-norepinephrine reuptake inhibitors (SNRIs) (e.g., Cymbalta, Effexor, Pristiq).

In an embodiment, for the treatment of Alzheimer's disease, the second therapeutic agent may be a cholinergic selected from the group consisting of:
- Physostigmine
- Neostigmine (Prostigmin, Vagostigmin)
- Pyridostigmine
- Ambenonium (Mytelase)
- Rivastigmine (Exelon)
- Galantamine (Nivalin, Razadyne, Razadyne ER, Reminyl, Lycoremine)
- Tacrine (Cognex)
- Donepezil (Aricept)

In a further embodiment the second therapeutic agent is an antipsychotic selected from the atypical antiphsychotic group consisting of:
- Amisulpride (Amazeo, Solian, Sulpitac, Amitrex, Soltus)
- Aripiprazole (Abilify, Aripiprex)
- Asenapine (Saphris, Sycrest)
- Blonanserin (Lonasen)
- Clotiapine (Entumine)
- Clozapine (Clozaril, Azaleptin, Leponex, Fazaclo, Froidir; Denzapine, Zaponex, Klozapol, Clopine)
- Iloperidone (Zomaril, Fanapt)
- Lurasidone (Latuda)
- Mosapramine (Cremin)
- Olanzapine (Zyprexa)
- Paliperidone (Invega)
- Perospirone (Lullan)
- Quetiapine (Seroquel, Ketipinor)
- Remoxipride (Roxiam)
- Risperidone (Risperdal)
- Sertindole (Serdolect, Serlect)
- Sulpiride (Sulpirid, Eglonyl)
- Ziprasidone (Geodon, Zeldox)
- Zotepine (Nipolept, Losizopilon, Lodopin, Setous)

In a further embodiment the second therapeutic agent is a SSRI selected from the following:
- citalopram (Celexa, Cipramil, Cipram, Dalsan, Recital, Emocal, Sepram, Seropram, Citox, Cital)
- dapoxetine (Priligy)
- escitalopram (Lexapro, Cipralex, Seroplex, Esertia)
- fluoxetine (Prozac, Fontex, Seromex, Seronil, Sarafem, Ladose, Motivest, Flutop, Fluctin (EUR), Fluox (NZ), Depress (UZB), Lovan (AUS), Prodep (IND))
- fluvoxamine (Luvox, Fevarin, Faverin, Dumyrox, Favoxil, Movox)
- paroxetine (Paxil, Seroxat, Sereupin, Aropax, Deroxat, Divarius, Rexetin, Xetanor, Paroxat, Loxamine, Deparoc)
- sertraline (Zoloft, Lustral, Serlain, Asentra)
- vilazodone (Viibryd)

In another embodiment the second therapeutic agent is a tetracyclic antidepressant (TeCA) selected from the group consisting of:
- Amoxapine (Amokisan, Asendin, Asendis, Defanyl, Demolox, Moxadil)
- Maprotiline (Deprilept, Ludiomil, Psymion)
- Mazindol (Mazanor, Sanorex)
- Mianserin (Bolvidon, Depnon, Norval, Tolvon)
- Mirtazapine (Remeron, Avanza, Zispin, Miro)
- Setiptiline (Tecipul)

In another embodiment the second therapeutic agent is a serotonin-noradrenaline reuptake inhibitor (SNRI) selected from the group consisting of:
- Desvenlafaxine (Pristiq)
- Duloxetine (Cymbalta, Ariclaim, Xeristar, Yentreve, Duzela)
- Milnacipran (Ixel, Savella, Dalcipran, Toledomin)
- Venlafaxine (Effexor, Efexor)

In another embodiment the second therapeutic agent is a Noradrenaline reuptake inhibitor (NRI) selected from the group consisting of
- Atomoxetine (Tomoxetine, Strattera, Attentin)
- Mazindol (Mazanor, Sanorex)
- Reboxetine (Edronax, Norebox, Prolift, Solvex, Davedax, Vestra)
- Viloxazine (Vivalan, Emovit, Vivarint, Vicilan)

In another embodiment the second therapeutic agent is a monoamine oxidase inhibitor (MAOI) selected from the group consisting of:
- Benmoxin (Nerusil, Neuralex)
- Hydralazine (Apresoline)
- Iproclozide (Sursum)
- Iproniazid (Marsilid, Iprozid, Ipronid, Rivivol, Propilniazida)
- Isocarboxazid (Marplan)
- Isoniazid (Laniazid, Nydrazid)
- Mebanazine (Actomol)
- Nialamide (Niamid)
- Octamoxin (Ximaol, Nimaol)
- Phenelzine (Nardil, Nardelzine)
- Pheniprazine (Catron)
- Phenoxypropazine (Drazine)

Pivalylbenzhydrazine (Tersavid)
Procarbazine (Matulane, Natulan, Indicarb)
Caroxazone (Surodil, Timostenil)
Echinopsidine (Adepren)
Furazolidone (Furoxone, Dependal-M)
Linezolid (Zyvox, Zyvoxam, Zyvoxid)
Tranylcypromine (Parnate, Jatrosom)
Brofaromine (Consonar)
Metralindole (Inkazan)
Minaprine (Cantor)
Moclobemide (Aurorix, Manerix)
Pirlindole (Pirazidol)
Toloxatone (Humoryl)
Lazabemide (Pakio, Tempium)
Pargyline (Eutonyl)
Rasagiline (Azilect)
Selegiline (Deprenyl, Eldepryl, Emsam)

In another embodiment the second therapeutic agent is a tricyclic antidepressant (TCA) selected from the group consisting of:
Amitriptyline (Tryptomer, Elavil, Tryptizol, Laroxyl, Sarotex, Lentizol)
Butriptyline (Evadene, Evadyne, Evasidol, Centrolese)
Clomipramine (Anafranil)
Desipramine (Norpramin, Pertofrane)
Dosulepin (Prothiaden, Dothep, Thaden and Dopress)
Doxepin (Aponal, Adapine, Doxal, Deptran, Sinquan, Sinequan, Zonalon, Xepin, Silenor)
Imipramine (Antideprin, Deprimin, Deprinol, Depsol, Depsonil, Dynaprin, Eupramin, Imipramil, Irmin, Janimine, Melipramin, Surplix, Tofranil)
Lofepramine (Gamanil, Tymelyt, Lomont)
Nortriptyline (Sensoval, Aventyl, Pamelor, Norpress, Allegron, Noritren, Nortrilen)
Protriptyline (Vivactil)
Trimipramine (Surmontil, Rhotrimine, Stangyl)

In certain embodiments, the second therapeutic agent is an atypical antidepressant, such as bupropion.

In certain embodiments, the second therapeutic agent is a mood stabilizer, such as lithium, sodium valproate, or valproic acid.

In certain embodiments, the second therapeutic agent is an acetylcholinesterase inhibitor, such as donepezil, galantamine, or rivastigmine.

In certain embodiments, the second therapeutic agent is a hormone, such as estrogen or progestogen.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, German 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The active ingredient can be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quarternary ammonium salts such as $N^+(C_{1-4}\text{alkyl})_4$ are also included.

When a provided compound is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, carbonic, boric, sulfamic, propionic, butyric, hydroxymaleic, mucic, phenylacetic, sulfanilic, aspartic, edetic, stearic, palmitic, oleic, lauric, ascorbic, valeric, perchloric, malonic, p-toluenesulfonic acid and the like. Particular embodiments include citric, hydrobromic, hydrochloric, maleic, phosphoric, sulfuric and tartaric acids. Other exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, palmoate (i.e., 1,1'-methylene-bis-(2-hydroxy-3-naphthoate)), adipate, alginate, ascorbate, aspartate, cyclopentanepropionate, borate, butyrate, camphorate, digluconate, dodecylsulfate, ethanesulfonate, glucoheptonate, glycerophosphate, hemisulfate, heptanoate, hexanoate, 2-hydroxyethanesulfonate, lactobionate, laurate, lauryl sulphate, malonate, 2-naphthalenesulfonate, nicotinate, pectinate, persulfate, 3-phenylpropionate, picrate, pivalate, propionate, stearate, thiocyanate, undecanoate, and valerate salts.

The preparation of the pharmaceutically acceptable salts described above and other typical pharmaceutically acceptable salts is more fully described by Berge et al., "Pharmaceutical Salts," *J. Pharm. Sci.*, 1977:66:1-19.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of a compound of formula (I), (Ia), (Ib), or (Ic) is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group (for instance at the $R_3$ position) is converted into an ester, such as an acetate or phosphate ester, or where a free amino group is (for instance at the $R_3$ position) converted into an amide (eg. α-aminoacid amide). Procedures for esterifying, e.g., acylating, the compounds of the invention are well known in the art and may include treatment of the compound with an appropriate carboxylic acid, anhydride or chloride in the presence of a suitable catalyst or base. In an embodiment the prodrug is a disodium phosphate ester. The disodium phosphate ester may be prepared in accordance with the methodology described in Pettit, G. R., et al, *Anticancer Drug Des.*, 1995, 10, 299.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres, e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

Unless otherwise stated, structures depicted herein are also meant to include compounds that differ only in the presence of one or more isotopically enriched atoms. For example, compounds having the present structures with the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

The synthetic methods and processes described herein to prepare the compounds of the present invention are amenable to solid phase synthetic techniques and/or combinatorial chemistry to produce individual compounds or libraries of compounds.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Synthetic Protocols

Example 1

A. Preparation of 6-(2,3-dihydro-1H-inden-2-ylamino)-2-methyl-4-phenylquinoline-3-carboxylic acid (Example 1)

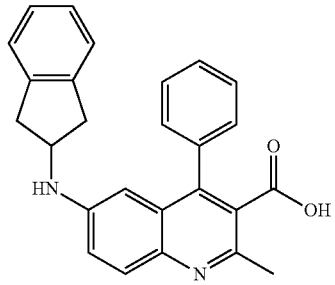 [SMILES: Cc1nc2ccc(NC3Cc4ccccc4C3)cc2c(-c2ccccc2)c1C(=O)O]

Step 1: tert-Butyl 2-methyl-6-nitro-4-phenylquinoline-3-carboxylate: A mixture of 2-amino-5-nitrobenzophenone (2 g, 8.26 mmol), $H_2NSO_3H$ (0.09 g, 0.93 mmol) and tert-butyl acetoacetate (3 ml, 18 mmol) was stirred for 1 h at 120° C. under $N_2$. To it, more of $H_2NSO_3H$ (0.04 g, 0.41 mmol) was added and stirring was continued at 120° C. until all 2-amino-5-nitrobenzophenone was consumed (about 3 h). After cooling to room temperature the solid material formed was dispersed in MeOH (20 ml) and filtered off, washed with fresh MeOH and dried to give pure product as a creamy solid (1.6 g, 53%). $^1$H NMR (300 MHz, $CDCl_3$) δ 8.41-8.5(m, 2H, 8.15 (d, J=9 Hz, 1H), 7.52-7.55(m, 3H), 7.3-7.4 (m, 2H), 2.82(s, 3H), 1.24(s, 9H).

Step 2: tert-Butyl 6-amino-2-methyl-4-phenylquinoline-3-carboxylate: A mixture of the product of Step 1 (1.05 g, 3.25 mmol) and 10% Pd/C (0.222 g, 32.5) in EtOAc was degassed under reduced pressure and saturated with $H_2$ gas. The resulting mixture was stirred overnight under $H_2$ balloon at room temperature, filtered through Celite bed and filtrate evaporated to dryness to give product as an yellowish solid (1.46 g, 98%), which was used in next step without further purification. $^1$H NMR (300 MHz, $CDCl_3$) δ 7.83 (d, J=8.9 Hz, 1H), 7.43-7.48(m, 3H), 7.27-7.34(m, 2H), 7.10 (dd, J=2.5, 8.9 Hz, 1H), 6.55(d, J=2.5 Hz, 1H), 3.79(broad s, 2H), 2.69(s, 3H), 1.2(s, 9H).

Step 3: tert-Butyl 6-(2,3-dihydro-1H-inden-2-ylamino)-2-methyl-4-phenylquinoline-3-carboxylate: A method of Abdel-Magid et al (J. Org. Chem., 61, 3849, 1996) was used: Glacial AcOH (0.25 ml) was added to a solution of the product of Step 2 (1.46 g, 4.4 mmol), 1H-inden-2(3H)-one (0.46 g, 4.5 mmol) and $NaBH(OAc)_3$ (1.4 g, 6.55 mmol) in anhydrous 1,2-dichloroethane (17 ml). The resulting mixture was stirred overnight at room temperature under $N_2$ and to it more of $NaBH(OAc)_3$ (0.4 g, 1.9 mmol) was added. After 2 h of stirring at room temperature, the mixture was quenched by addition of 1N NaOH aq (5 ml). This was diluted to 60 ml with $Et_2O$ and washed with $H_2O$ and brine. The organic phase was dried over anhydrous $MgSO_4$, filtered and filtrate evaporated to dryness under reduced pressure. The residue was purified by flash column chromatography ($SiO_2$, $CH_2Cl_2$) to give pure product as a creamy solid (1.4 g, 71%). $^1$H NMR (300 MHz, $CDCl_3$) δ 7.83 (d, J=9.0 Hz, 1H), 7.34-7.5(m, 5H), 7.12-7.21 (m, 4H), 7.05(dd, J=2.6, 9.0 Hz, 1H), 6.49(d, J=2.6 Hz, 1H), 4.17(m, 1H), 4.08(m, 1H), 3.19-3.27(m 2H), 2.73-2.83(m, 2H), 2.7(s, 3H), 1.22(s, 9H).

Step 4: 6-(2,3-dihydro-1H-inden-2-ylamino)-2-methyl-4-phenylquinoline-3-carboxylic acid: A mixture of the product of Step 3 (1.4 g, 3.1 mmol), in anhydrous $CF_3COOH$ (3 ml) was stirred for 24 h at room temperature under $N_2$, than evaporated to dryness under reduced pressure. The residue was dried in vacuo for 1 h and suspended in $H_2O$ (10 ml) and the pH of the mixture was adjusted to ~8 with $NH_4OH$. This was filtered and filtrate was partially evaporated under reduced pressure. The precipitate formed was filtered off, washed with $H_2O$, small volume of EtOH, $Et_2O$ and dried in vacuo to give pure product as a deep yellow solid (1.09 g, 89%). $^1$H NMR (300 MHz, DMSO-$d_6$) δ 7.69 (d, J=9.0 Hz, 1H), 7.3-7.5(m, 5H), 7.06-7.2(m, 5H), 6.42(m, 1H), 6.28(d, J=2.4 Hz, 1H), 3.93(m, 1H), 3.08(dd, J=7.0, 16 Hz, 2H), 2.72(dd, J=7.0, 16 Hz, 2H), 2.55(s, 3H). LCMS, >99%, m/z (%): 395 ($M^{+\cdot}$, 100).

B. Alternative preparation of 6-(2,3-dihydro-1H-inden-2-ylamino)-2-methyl-4-phenylquinoline-3-carboxylic acid (Example 1)

Step 1: Methyl 2-methyl-6-nitro-4-phenylquinoline-3-carboxylate: A mixture of 2-amino-5-nitrobenzophenone (1 g, 4.1 mmol), $H_2NSO_3H$ (0.04 g, 041 mmol) and methyl acetoacetate (1.11 ml, 10.3 mmol) was stirred overnight at 120° C. under $N_2$, than cooled to room temperature, diluted to 100 ml with EtOAc and washed with $H_2O$. The organic phase was dried over anhydrous $MgSO_4$, filtered and filtrate evaporated to dryness under reduced pressure. The residue was purified by crystallization from EtOH to give pure product as a creamy solid (1.05 g, 80%). $^1$H NMR (300 MHz, $CDCl_3$) δ 8.52 (d, J=2.5 Hz, 1H), 8.48 (dd, J=2.5, 9.2 Hz, 1H), 7.53(m, 3H), 7.34(m, 2H), 3.59(s, 3H), 2.8(s, 3H).

Step 2: Methyl 6-amino-2-methyl-4-phenylquinoline-3-carboxylate: 10% palladium on carbon (0.22 g) was added to a solution of the product of Step 1 (1.05 g, 3.25 mmol) and ammonium formate (2.05 g, 32.5 mmol) in MeOH/THF mixture (1:1, 125 ml) under $N_2$. The resulting mixture was stirred for 30 min at room temperature, filtered through Celite bed and filtrate evaporated to dryness. The residue was diluted to 50 ml with $CH_2Cl_2$, washed with $H_2O$, dried over anhydrous $MgSO_4$, filtered and filtrate evaporated to dryness to give the title product as a heavy oil (0.91 g, 98%), which was used in next step without further purification. $^1$H NMR (300 MHz, $CDCl_3$) δ 7.86 (d, J=8.9 Hz, 1H), 7.44(m, 3H), 7.31(m, 2H), 7.13 (dd, J=2.5, 8.9 Hz, 1H), 6.61(d, J=2.5 Hz, 1H), 3.78 (broad s, 2H), 3.53(s, 3H), 2.67(s, 3H).

Step 3: Methyl 6-(2,3-dihydro-1H-inden-2-ylamino)-2-methyl-4-phenylquinoline-3-carboxylate: A method of Abdel-Magid et al (J. Org. Chem., 61, 3849, 1996) was used: Glacial AcOH (0.2 ml) was added to a solution of the product of Step 2 (0.91 g, 3.31 mmol), 1H-inden-2(3H)-one (0.41 g, 3.31 mmol) and NaBH(OAc)$_3$ (1.05 g, 4.9 mmol) in anhydrous 1,2-dichloroethane (12.5 ml). The resulting mixture was stirred overnight at room temperature under N$_2$ than quenched by addition of 1N NaOH aq (1 ml). This was diluted to 60 ml with Et$_2$O and washed with N$_2$. The organic phase was dried over anhydrous MgSO$_4$, filtered and filtrate evaporated to dryness under reduced pressure. The residue was purified by flash column chromatography (SiO$_2$, CH$_2$Cl$_2$) to give pure product as a yellow solid (0.98 g, 72%). $^1$H NMR (300 MHz, CDCl$_3$) δ 7.84 (d, J=9.0 Hz, 1H), 7.34-7.49(m, 5H), 7.15-7.18(m, 4H), 7.07(dd, J=1.7, 9.0 Hz, 1H), 6.49(d, J=1.7 Hz, 1H), 4.11-4.18(m, 2H), 3.55(s, 3H), 3.2(dd, J=6.2, 16 Hz, 2H), 2.8(dd, J=6.2, 16 Hz, 2H), 2.68(s, 3H).

Step 4: 6-(2,3-dihydro-1H-inden-2-ylamino)-2-methyl-4-phenylquinoline-3-carboxylic acid: A mixture of the product of Step 3 (0.98 g, 2.4 mmol), 2MKOH aq (3.6 ml, 7.2 ml) and 18-crown-6 ether (0.63 g, 0.24 mmol) in EtOH (50 ml) was refluxed for 30 h under N$_2$. After cooling to room temperature the organic solvent was removed under reduced pressure and the residue was diluted to 5 ml with H$_2$O, filtered and the filtrate was acidified to pH~5 with 10% aqueous citric acid. The precipitate formed was filtered off, washed with H$_2$O, small volume of EtOH, Et$_2$O and dried in vacuo to give pure product as a deep yellow solid (0.89 g, 93%). $^1$H NMR (300 MHz, DMSO-d$_6$) δ 7.65 (d, J=9.0 Hz, 1H), 7.3-7.5(m, 5H), 7.06-7.18(m, 5H), 6.31(m, 1H), 6.28(d, J=2.4 Hz, 1H), 3.92 (m, 1H), 3.08(dd, J=7, 16 Hz, 2H), 2.72(dd, J=7 Hz, 16H), 2.48(s, 3H). LCMS, R$_t$=1.48 min, >99%, m/z (%): 395 (M$^{+\cdot}$, 100).

C. Alternative preparation of 6-(2,3-dihydro-1H-inden-2-ylamino)-2-methyl-4-phenylquinoline-3-carboxylic acid (Example 1)

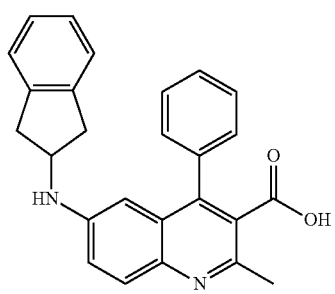 [SMILES: Cc1nc2ccc(NC3Cc4ccccc4C3)cc2c(-c2ccccc2)c1C(=O)O]

Step 1: Ethyl 2-methyl-6-nitro-4-phenylquinoline-3-carboxylate: A mixture of 2-amino-5-nitrobenzophenone (1 g, 4.1 mmol), H$_2$NSO$_3$H (40 mg) and tert-butyl acetoacetate (1.3 ml, 10.3 mmol) was stirred for 12 h at 120° C. under N$_2$. After cooling to room temperature, the reaction mixture was diluted with ethyl acetate and washed with water. The organic layer was dried (MgSO$_4$) and concentrated in vacuo to give a solid, which was recrystallised from EtOH to give a pale orange solid (1.05 g, 76%). $^1$H NMR (300 MHz, CDCl$_3$) δ 8.41-8.5(m, 2H), 8.15 (d, J=9 Hz, 1H), 7.52-7.55(m, 3H), 7.3-7.4 (m, 2H), 2.82(s, 3H), 1.24(s, 9H).

Step 2: Ethyl 6-amino-2-methyl-4-phenylquinoline-3-carboxylate: A mixture of the product of Step 1 (1.05 g, 3.25 mmol) and 10% Pd/C (0.222 g, 32.5) in EtOAc was degassed under reduced pressure and saturated with H$_2$ gas. The resulting mixture was stirred overnight under H$_2$ balloon at room temperature, filtered through Celite bed and filtrate evaporated to dryness to give product as an yellowish solid (1.46 g, 98%), which was used in next step without further purification. $^1$H NMR (300 MHz, CDCl$_3$) δ 7.83 (d, J=8.9 Hz, 1H), 7.43-7.48(m, 3H), 7.27-7.34(m, 2H), 7.10 (dd, J=2.5, 8.9 Hz, 1H), 6.55(d, J=2.5 Hz, 1H), 3.79(broad s, 2H), 2.69(s, 3H), 1.2(s, 9H).

Step 3: Ethyl 6-(2,3-dihydro-1H-inden-2-ylamino)-2-methyl-4-phenylquinoline-3-carboxylate: A method of Abdel-Magid et al (J. Org. Chem., 61, 3849, 1996) was used: Glacial AcOH (0.25 ml) was added to a solution of the product of Step 2 (1.46 g, 4.4 mmol), 1H-inden-2(3H)-one (0.46 g, 4.5 mmol) and NaBH(OAc)$_3$ (1.4 g, 6.55 mmol) in anhydrous 1,2-dichloroethane (17 ml). The resulting mixture was stirred overnight at room temperature under N$_2$ and to it more of NaBH(OAc)$_3$ (0.4 g, 1.9 mmol) was added. After 2 h of stirring at room temperature, the mixture was quenched by addition of 1N NaOH aq (5 ml). This was diluted to 60 ml with Et$_2$O and washed with H$_2$O and brine. The organic phase was dried over anhydrous MgSO$_4$, filtered and filtrate evaporated to dryness under reduced pressure. The residue was purified by flash column chromatography (SiO$_2$, CH$_2$Cl$_2$) to give pure product as a creamy solid (1.4 g, 71%). $^1$H NMR (300 MHz, CDCl$_3$) δ 7.83 (d, J=9.0 Hz, 1H), 7.34-7.5(m, 5H), 7.12-7.21 (m, 4H), 7.05(dd, J=2.6, 9.0 Hz, 1H), 6.49(d, J=2.6 Hz, 1H), 4.17(m, 1H), 4.08(m, 1H), 3.19-3.27(m 2H), 2.73-2.83(m, 2H), 2.7(s, 3H), 1.22(s, 9H).

Step 4: 6-(2,3-dihydro-1H-inden-2-ylamino)-2-methyl-4-phenylquinoline-3-carboxylic acid: A mixture of the product of Step 3 (1.4 g, 3.1 mmol), in anhydrous CF$_3$COOH (3 ml) was stirred for 24 h at room temperature under N$_2$, than evaporated to dryness under reduced pressure. The residue was dried in vacuo for 1 h and suspended in H$_2$O (10 ml) and the pH of the mixture was adjusted to ~8 with NH$_4$OH. This was filtered and filtrate was partially evaporated under reduced pressure. The precipitate formed was filtered off, washed with H$_2$O, small volume of EtOH, Et$_2$O and dried in vacuo to give pure product as a deep yellow solid (1.09 g, 89%). $^1$H NMR (300 MHz, DMSO-d$_6$) δ 7.69 (d, J=9.0 Hz, 1H), 7.3-7.5(m, 5H), 7.06-7.2(m, 5H), 6.42(m, 1H), 6.28(d, J=2.4 Hz, 1H), 3.93(m, 1H), 3.08(dd, J=7.0, 16 Hz, 2H), 2.72(dd, J=7.0, 16 Hz, 2H), 2.55(s, 3H). MS m/z M$^+$ 395.

Example 2

Preparation of 6-(2,3-Dihydro-1H-inden-2-ylamino)-1-ethyl-3-(morpholin-4-ylcarbonyl)-1,8-naphthyridin-4(1H)-one (Example 2)

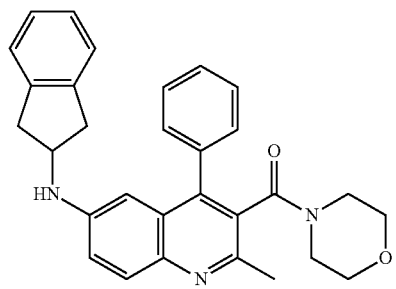 [SMILES: Cc1nc2ccc(NC3Cc4ccccc4C3)cc2c(-c2ccccc2)c1C(=O)N1CCOCC1]

Thionyl chloride (1 mL) was added to a suspension of 6-(2,3-dihydro-1H-inden-2-ylamino)-2-methyl-4-phenylquinoline-3-carboxylic acid (150 mg, 0.37 mmol) in DCM (5 mL) and the reaction mixture was stirred at room temperature for 1 h. The solvent was removed in vacuo and the resulting residue dissolved in DCM (5 mL). Morpholine (0.32 mL, 3.7 mmol) was added and the solution was stirred for 1 h. The reaction mixture was partitioned over DCM and 10% aqueous citric acid solution. The organics were dried over $MgSO_4$ and concentrated in vacuo to give a yellow residue. The crude was purified by flash column chromatography ($SiO_2$, 1:1 $CH_2Cl_2$/EtOAc) to give a bright yellow solid (110 mg, 65%).

$^1$H NMR (300 MHz, DMSO-$d_6$) δ 7.94 (d, J=9.0 Hz, 1H), 7.38-7.57 (m, 5H), 6.99-7.20 (m, 5H), 6.57 (d, J=2.4 Hz, 1H), 4.18-4.26 (m, 2H)., 2.67-3.59 (m, 12H), 2.67 (s, 3H). MS m/z $M^+$ 464.4.

Biological Data
Screening of the Anxiolytic Effect
Light Dark Test

The light dark paradigm is based on a conflict between the innate aversion of rodents to brightly illuminated areas and on the spontaneous exploratory behaviour of the mice. If given a choice between a large brightly compartment versus a small dark compartment they spontaneously prefer the dark part. Anxiolytic compounds have been found to increase the number of entries into the bright compartment and the total time spent there. Anxiogenic compounds were observed to work in the opposite way.

The apparatus consists of two PVC (polyvinylchloride) boxes (19×19×15 cm) covered with Plexiglas. One of these boxes is darkened. The other box is illuminated by 100 W desk lamp placed 15 cm above and providing an illumination of about 4400 Lux. An opaque plastic tunnel (5×7×10 cm) separates the dark box from the illuminated one.

Animals were placed individually in the lit box, with head directed towards the tunnel. The time spent in the lit box and the number of transitions between the two boxes was recorded over a 5 min period after the first entry of the animal in the dark box. The total walked distance in the lit box was also recorded. Animals scored without entry into the lit box were excluded from the analysis.

Test Compounds and Treatment

Test compound was prepared in aqueous vehicle containing 0.5% w/v hydroxypropylmethyl cellulose, 0.5% v/v benzyl alcohol and 0.4% v/v Tween 80. It was administrated per os 1 hour before the implementation of the test.

N=10-12 mice

Elevated Plus Maze

The Elevated Plus Maze (EPM) situation rests on the conflict between the innate tendencies of rodents to explore novel environments and avoid open and brightly lit areas. In this task the mouse is placed in the centre of the maze. From here it can walk down any of four runways. Two of the arms are well lit and open, and the other two are enclosed and dimly lit. Mice prefer the closed arms but will venture out into the open arms. The amount of time spent in the open arms and the number of times the mice enter the open arms are recorded. The total walked distance in the open arms is also recorded. "Anxious" mice will spend little time in the open arms and make very few entries into the open arms.

The apparatus is made of polyvinylchloride materials and consists of four equal exploratory arms (45×10 cm) which are all interconnected by a small platform (10×10 cm). Two arms are open and two others are closed with walls (30 cm high). The apparatus is placed 66 cm above the floor. A videotracking system is used to record the test (ViewPoint, France). The video camera is placed at 2.50 m above the equipment and connected to the computer via a video capture card (Pinnacle Systems, France).

A trial consists of placing an animal on the central platform facing a closed arm. The number of entries and the duration spent in open arms are automatically recorded by a videotrack system during an 5 minutes period.

The apparatus is cleaned between each animal using alcohol (70%).

Test Compounds and Treatment

Test compound was prepared in aqueous vehicle containing 0.5% w/v hydroxypropylmethyl cellulose, 0.5% v/v benzyl alcohol and 0.4% v/v Tween 80. It was administrated per os 1 hour before the implementation of the test.

N=10-12 rats

Marble Burying

The Marble Burying test is used as a model for both anxiety and obsessive compulsive disorders. Mice have a natural tendency to bury marbles under the bedding when placed in a cage with rows of evenly spaced marbles on the floor. Suppression of this spontaneous burying has been used as a measure of anxiolytic drug action. Mice pre-treated with benzodiazepines and different classes of antidepressants bury less marbles when compared to the control mice The apparatus consists of transparent polycarbonate cages (30 cm×18 cm×19 cm) containing a 5 cm layer of fine sawdust bedding and 20 glass marbles (diameter: 1.5 cm) spaced evenly along the walls of the cage. Each animal is placed individually in the cage where it remains for a 20 min test session. On termination of the test session the animals are removed from the cage and the number of marbles at least two-thirds buried in the sawdust is recorded.

Test Compounds and Treatment

Test compound was prepared in aqueous vehicle containing 0.5% w/v hydroxypropylmethyl cellulose, 0.5% v/v benzyl alcohol and 0.4% v/v Tween 80. It was administrated per os 1 hour before the implementation of the test.

N=10-12 mice

Screening of the Sedative or Stimulating Effect of Compounds in the Modified Open Field The open field (dark) is used to measure the spontaneous motor activity of mice in a quiet, dark environment. This system is useful for discriminating the sedating or stimulating properties of test compounds on spontaneous locomotion and can thus provide a preliminary indication of potentially adverse effects such as sedation.

The apparatus is an open plexiglass cage (52×52 cm) with 40 cm walls. The animal's movements are tracked by a computerised video tracking system, consisting of an overhead camera, diode sensors placed underneath the floor of the cage, computer and video analyser software (ViewPoint, France). The video camera is placed at 2.50 m above the cage and connected to the computer via a video capture card (Pinnacle Systems, France). The video tracking system is set in a way that the floor of the OF is divided into nine equal squares. The total number of crossed squares and the total walked distance are recorded.

Each animal is singly placed in a corner of the apparatus and its locomotor activity is automatically recorded over a period of 20 minutes.

The apparatus is cleaned between each animal with alcohol (70%).

Test Compounds and Treatment

Test compound was prepared in aqueous vehicle containing 0.5% w/v hydroxypropylmethyl cellulose, 0.5% v/v ben zyl alcohol and 0.4% v/v Tween 80. It was administered per os 1 hour before the implementation of the test.

N=10-12 mice

Screening of the Antidepressant Properties of the Compound(s) in the Mouse Forced Swim Test The forced swim test is the most widely used paradigm for the evaluation of potential antidepressant effect of drugs. Animals placed in a container filled with water show periods of increased swimming activity and periods of relative immobility. Immobile posture reflects a state of tiredness, fatigue, reduced stamina or a lowered mood (hopelessness) similar to the core symptoms observed in depressed patients and in individuals under intense stress. Clinically active anti-depressants have been found to delay the onset of the first phase of immobility and to reduce the total time of relative immobility. The test has some predictive value for anti-depressant drugs. The apparatus consists of a glass cylinder (height 35 cm; diameter 24 cm) filled with water (depth: 25 cm, temperature: 25±1° C.).

3. Evaluation of Neurite Outgrowth

After the 3 days exposure of the neurons to the test compounds, cultures were washed with phosphate-buffered saline (PBS, Gibco) and fixed using 2.5% glutaraldehyde in PBS. Several pictures (~80) of neurons with neurites without any branching were taken per condition using a digital camera (Coolpix 995; Nikon) mounted on the microscope (Nikon, objective 40x). Neurites were outlined on computer screen using imaging software (Image-Pro Plus, France), which automatically calculates the length.

4. Statistical Analysis

A global analysis of the data was performed using a one way analysis of variance (ANOVA), followed by Fisher's Protected Least Significant Difference when applicable. The level of significance was set to $p<0.05$. All results were expressed as mean±sem. N=~180 cells Compounds were tested at 1 nM, 10 nM and 100 nM on two independent cultures comprising 2 Petri dishes per culture and per condition. In parallel, BDNF was tested at 50 ng/ml.

TABLE 1

| Example Number | Light Dark Box mice | Open Field (Dark) mice | Elevated Plus Maze rat | Marble Burying mice | Forced Swim Test mice | Neurite outgrowth |
|---|---|---|---|---|---|---|
| 1 | MED 0.1 mg/kg | Tested at 5-100 mg/kg No Sedation at any dose | MED 0.1 mg/kg | MED 0.1 mg/kg | MED 10 mg/kg | Significant effect at concentrations ≤100 nM |
| 2 | MED 10 mg/kg | | | | | |

MED—Minimum Effective Dose

Test Compounds and Treatment

Test compound was prepared in aqueous vehicle containing 0.5% w/v hydroxypropylmethyl cellulose, 0.5% v/v benzyl alcohol and 0.4% v/v Tween 80. It was administered per os 1 hour before the implementation of the test.

N=10-12 mice.

Screening of the Neurotrophic Properties of the Compound(s) in the Neurite Outgrowth Assay Cortical Neurons Culture Female rats of 17 days gestation were killed by cervical dislocation and the foetuses were removed from the uterus. Their brains were placed in ice-cold medium of Leibovitz (L15, Gibco, Fisher bioblock, France). Cortex were dissected and meninges were carefully removed. The cortical neurons were dissociated by trypsinization for 30 min at 37° C. (trypsin-EDTA Gibco) in presence of 0.1 mg/ml DNAse I (Roche, France). The reaction was stopped by addition of Dulbecco's Modified Eagle Medium (DMEM; Gibco) with 10% of fetal bovine serum (FBS; Gibco). The suspension was triturated with a 10-ml pipette and using a 21G needle and syringe, and centrifuged at 350×g for 10 min at room temperature. The pellet of dissociated cells was resuspended in medium consisting of Neurobasal (Gibco) supplemented with 2% B27 supplement (Gibco), 0.5 mM L-Glutamine (Gibco), an antibiotic-antimicotic mixture. Viable cells were counted in a Neubauer cytometer using the trypan blue exclusion test (Sigma). Cells were seeded on the basis of 30000 cells per Petri dish (ø35 mm, Nunc) precoated with poly-L-lysine.

2. Treatment

Cells were allowed to adhere 2 h and maintained in a humidified incubator at 37° C. in 5% $CO_2$-95% air atmosphere. After neuronal adhesion (2 h after the plating), cultures were exposed to Example 1 or BDNF for a period of 3 days.

5. Solubility, logD and Metabolic Stability Data for Example 1

| Parameter | Example 1 |
|---|---|
| Structure | |
| Appearance | Yellow solid |
| Molecular Weight | 394 |
| Solubility (kinetic, ug/mL) | 50-100 (pH 6.5), 25-50 (pH 2) |
| $logD_{7.4}$ | 2.0 |
| PSA ($A^2$) | 62 |
| in vitro HLM (mL/min/µg protein) | 0.008 |
| in vitro $CL_{int}$ RLM (mL/min/µg protein) | 0.010 |

The invention claimed is:
1. A compound of formula (I) or salt thereof;

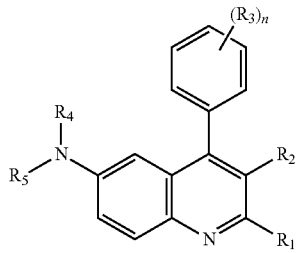

(I)

wherein
- $R_1$ represents hydrogen, or optionally substituted $C_1$-$C_6$ alkyl;
- $R_2$ represents —C(O)NR'R'' (where R' is —H or optionally substituted $C_1$-$C_6$ alkyl and R'' is optionally substituted $C_1$-$C_6$ alkyl, —OH or —CN, or R' and R'' together form an optionally substituted heterocyclyl), —C(O)OR' (where R' is —H or optionally substituted $C_1$-$C_6$ alkyl), —C(O)NHSO$_2$R''' (where R''' is optionally substituted aryl or optionally substituted $C_1$-$C_6$ alkyl), —S(O)$_2$NHR'''' (where R'''' is —H, optionally substituted $C_1$-$C_6$ alkyl, or optionally substituted aryl), optionally substituted heteroaryl or optionally substituted heterocyclyl;
- $R_3$ represents carboxyl, cyano, dihalomethoxy, halogen, hydroxy, nitro, pentahaloethyl, phosphono, phosphorylamino, phosphinyl, sulfo, trihaloethenyl, trihaloethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, or optionally substituted thioacylamino;
- $R_4$ represents H, optionally substituted alkyl, optionally substituted aryl, optionally substituted cycloalkyl, optionally substituted acyl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl;
- $R_5$ represents optionally substituted cycloalkyl or optionally substituted cycloalkenyl; and
- n is 0 or an integer of 1 to 4, inclusive.

2. A compound according to claim 1 wherein the compound of formula (I) is a compound of formula (Ia) or salt thereof;

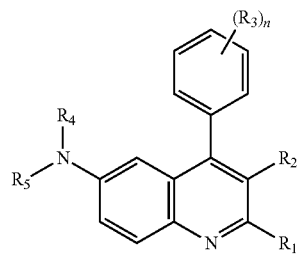

(Ia)

wherein
- $R_1$ represents $C_1$-$C_4$ alkyl;
- $R_2$ represents —C(O)NR'R'' (where R' is H or $C_1$-$C_4$ alkyl and R'' is $C_1$-$C_4$ alkyl, OH or CN), —C(O)OR' (where R' is H or $C_1$-$C_4$ alkyl), —C(O)NHSO$_2$R''' (where R''' is aryl or $C_1$-$C_3$ alkyl), —S(O)$_2$NHR'''' (where R'''' is H, $C_1$-$C_3$ alkyl, or aryl), optionally substituted heteroaryl or optionally substituted heterocyclyl;
- $R_3$ represents carboxyl, cyano, dihalomethoxy, halogen, hydroxy, nitro, pentahaloethyl, phosphono, phosphorylamino, phosphinyl, sulfo, trihaloethenyl, trihaloethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, or optionally substituted thioacylamino;
- $R_4$ represents H, optionally substituted alkyl, optionally substituted aryl, optionally substituted cycloalkyl, optionally substituted acyl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl;

$R_5$ represents optionally substituted cycloalkyl or optionally substituted cycloalkenyl; and n is 0 or an integer of 1 to 4, inclusive.

3. A compound according to claim 1, or a salt thereof, wherein $R_1$ is methyl or ethyl.

4. A compound according to claim 1, or a salt thereof, wherein $R_2$ represents —C(O)NR'R" (where R' is H or $C_1$-$C_4$ alkyl and R" is $C_1$-$C_4$ alkyl, OH or CN or R' and R" together form an optionally substituted heterocyclyl), —C(O)OH, —C(O)NHSO$_2$R'" (where R'" is aryl or $C_1$-$C_3$ alkyl), or —S(O)$_2$NHR"" (where R"" is H, $C_1$-$C_3$ alkyl, or aryl), optionally substituted heteroaryl, or optionally substituted heterocyclyl.

5. A compound according to claim 1 wherein $R_2$ is —C(O)NR'R" where R' and R" together form an optionally substituted morpholinyl.

6. A compound according to claim 1, or a salt thereof, wherein $R_2$ represents:

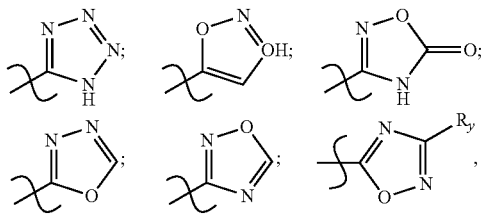

where $R_y$ is H or $C_{1-6}$ alkyl.

7. A compound according to claim 1, or a salt thereof, wherein $R_2$ represents —COOH.

8. A compound according to claim 1, or a salt thereof, wherein n is 0, 1 or 2.

9. A compound according to claim 8, or a salt thereof, wherein n is 1 and $R_3$ represents halogen, CN, CF$_3$, amino, hydroxyl, —NHC$_1$-C$_3$ alkyl, —N(C$_1$-C$_3$ alkyl)$_2$, —COOH, —COO(C$_1$-C$_3$ alkyl), phenyl, benzyl, C$_1$-C$_3$ alkyl or C$_1$-C$_3$ alkoxy.

10. A compound according to claim 1, or a salt thereof, wherein $R_4$ is H or $C_1$-$C_3$ alkyl.

11. A compound according to claim 1, or a salt thereof, wherein $R_5$ is:

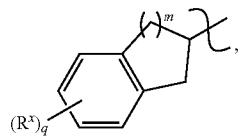

wherein
m is 1, 2, or 3;
q is 0, 1, 2, 3, or 4; and
$R^x$ is halo, —CN, —NO$_2$, —CO$_2$H, —CO$_2$C$_{1-6}$alkyl, —CONH$_2$, —CONH(C$_{1-6}$alkyl), —CONH(C$_{1-6}$alkyl)$_2$, —OH, hydroxyalkyl, alkoxy, alkyl, acyl, carboxyalkyl, acetyl, trifluoromethyl, benzyloxy, phenoxy, —NH$_2$, —NH(C$_{1-6}$alkyl) or —N(C$_{1-6}$alkyl)$_2$.

12. A compound according to claim 1, or a salt thereof, wherein $R_5$ is indanyl, optionally substituted 1 or 2 times by halo, CN, NO$_2$, CO$_2$H, CO$_2$C$_{1-6}$alkyl, CONH$_2$, CONH(C$_{1-6}$alkyl), CONH(C$_{1-6}$alkyl)$_2$, OH, hydroxyalkyl, alkoxy, alkyl, acyl, carboxyalkyl, acetyl, trifluoromethyl, benzyloxy, phenoxy, NH$_2$, NH(C$_{1-6}$alkyl) or NH(C$_{1-6}$alkyl)$_2$.

13. A compound according to claim 1, or a salt thereof, selected from:

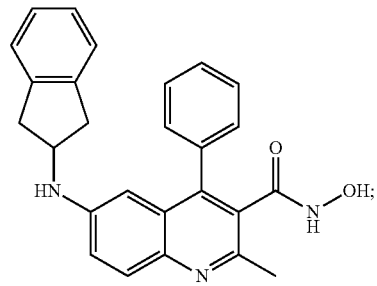

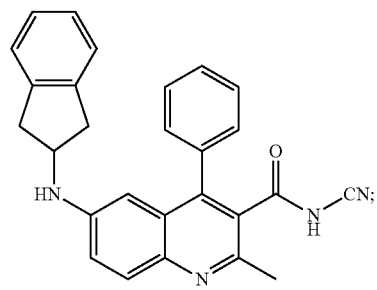

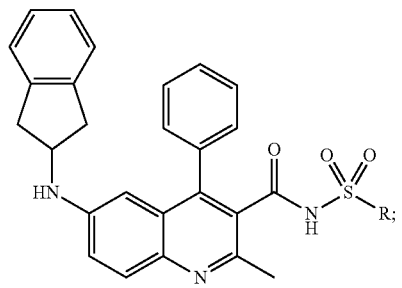

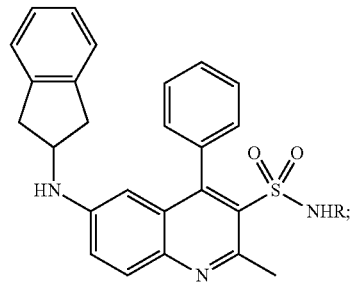

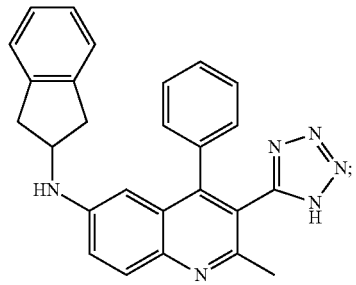

-continued

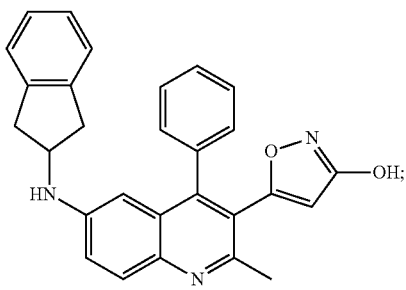

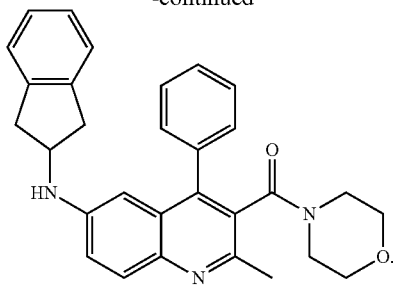

15. A compound according to claim 1, or a salt thereof, which is

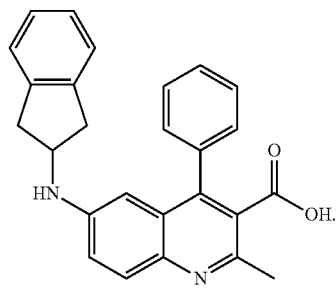 [SMILES: Cc1nc2ccc(NC3Cc4ccccc4C3)cc2c(-c2ccccc2)c1C(=O)O]

16. A pharmaceutical composition comprising a compound according to claim 1 and optionally a pharmaceutically acceptable excipient.

17. A method for treating anxiety including the step of administering to a patient in need thereof a compound according to claim 1 or a pharmaceutically acceptable salt thereof.

18. A method for treating depression including the step of administering to a patient in need thereof a compound according to claim 1 or a pharmaceutically acceptable salt thereof.

19. A method for preparing a compound of formula (II) or a salt thereof:

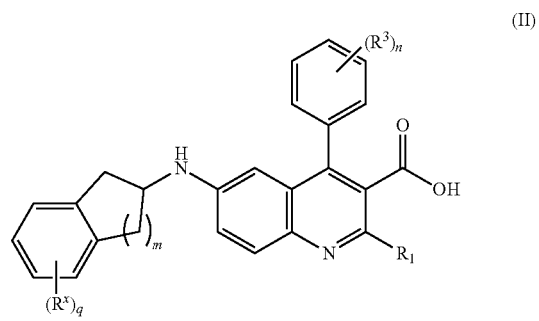

including the steps of:

(a) reacting a compound of formula

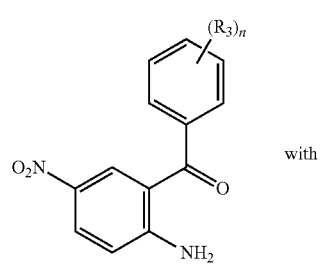

with and wherein R is H, aryl, or $C_{1-3}$ alkyl.

14. A compound according to claim 1, or a salt thereof, selected from:

-continued

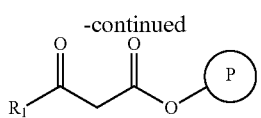

(where P is a protecting group)
to afford a compound of formula (IIa):

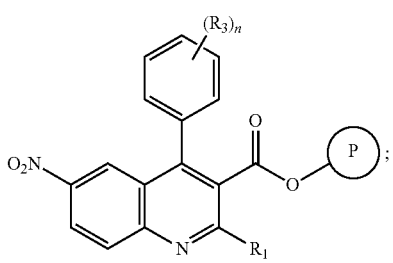

(IIa)

(b) subjecting a compound of formula (IIa) to reducing conditions to afford a compound of formula (IIb)

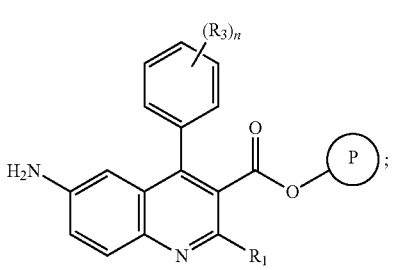

(IIb)

(c) reacting a compound of formula (IIb) with a compound of formula

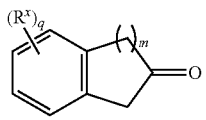

to afford a compound of formula (IIc)

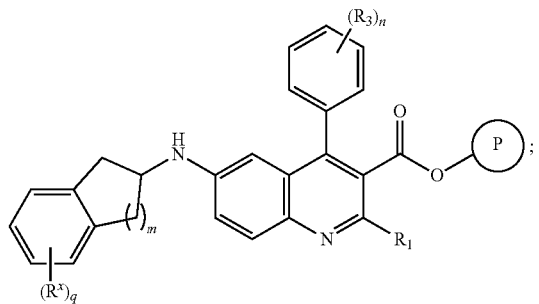

and (d) deprotecting a compound of formula (IIc) to afford a compound of formula (II), wherein $R_1$ represents hydrogen, or optionally substituted $C_1$-$C_6$ alkyl;

$R_3$ represents carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxycylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, or optionally substituted thioacylamino;

n is 0 or an integer of 1 to 4, inclusive;

m is 1, 2, or 3;

q is 0, 1, 2, 3 or 4; and $R^x$ is halo, —CN, —$NO_2$, —$CO_2H$, —$CO_2C_{1-6}$alkyl, —$CONH_2$, —CONH($C_{1-6}$alkyl), —CONH($C_{1-6}$alkyl)$_2$, —OH, hydroxyalkyl, alkoxy, alkyl, acyl, carboxyalkyl, acetyl, trifluoromethyl, benzyloxy, phenoxy, —$NH_2$, —NH($C_{1-6}$alkyl) or —N($C_{1-6}$alkyl)$_2$.

* * * * *

UNITED STATES PATENT AND TRADEMARK OFFICE
CERTIFICATE OF CORRECTION

PATENT NO. : 9,023,848 B2
APPLICATION NO. : 14/002243
DATED : May 5, 2015
INVENTOR(S) : Bernard Luke Flynn et al.

It is certified that error appears in the above-identified patent and that said Letters Patent is hereby corrected as shown below:

On The Title Page, insert item (30) Foreign Application Priority Data
-- Mar. 2, 2011 (AU) . . . . . . . . . . . . . . . . . . . . . . . . 2011900738 --.

In The Claims

In claim 6, at column 59, lines 22-25, the formula:

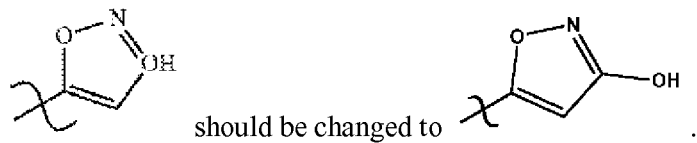

should be changed to

In claim 19, at column 62, lines 40-53, the formula:

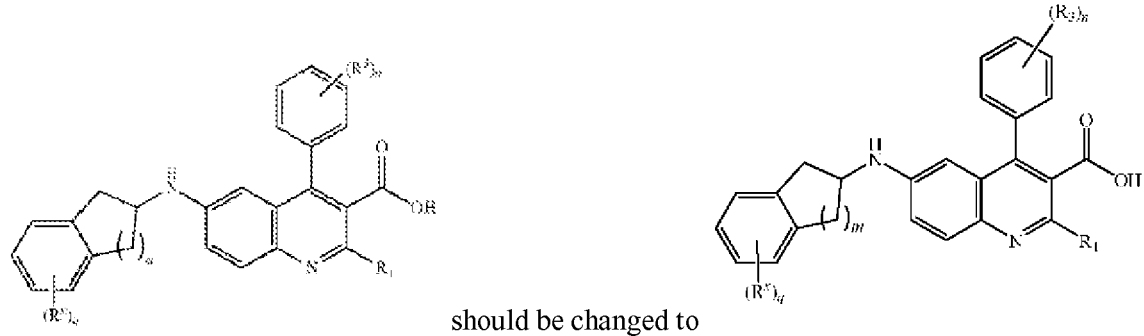

should be changed to

Signed and Sealed this
Ninth Day of February, 2016

Michelle K. Lee
*Director of the United States Patent and Trademark Office*